United States Patent
Lowe

(10) Patent No.: US 9,433,358 B2
(45) Date of Patent: Sep. 6, 2016

(54) METHOD AND APPARATUS FOR PRODUCING A CENTRAL PRESSURE WAVEFORM IN AN OSCILLOMETRIC BLOOD PRESSURE SYSTEM

(75) Inventor: Andrew Lowe, Auckland (NZ)

(73) Assignee: USCOM LTD., Sydney (AU)

( * ) Notice: Subject to any disclaimer, the term of this patent is extended or adjusted under 35 U.S.C. 154(b) by 946 days.

(21) Appl. No.: 12/632,003

(22) Filed: Dec. 7, 2009

(65) Prior Publication Data

US 2010/0152593 A1 Jun. 17, 2010

Related U.S. Application Data

(60) Provisional application No. 61/201,540, filed on Dec. 11, 2008.

(51) Int. Cl.
| | |
|---|---|
| *A61B 5/021* | (2006.01) |
| *A61B 5/029* | (2006.01) |
| *A61B 5/00* | (2006.01) |
| *G06K 9/00* | (2006.01) |
| *G06F 19/00* | (2011.01) |

(52) U.S. Cl.
CPC ............ *A61B 5/021* (2013.01); *A61B 5/02125* (2013.01); *A61B 5/412* (2013.01); *G06K 9/0053* (2013.01); *A61B 5/029* (2013.01); *G06F 19/3406* (2013.01)

(58) Field of Classification Search
CPC .. A61B 5/021; A61B 5/02125; A61B 5/029; A61B 5/412; G06F 19/3406; G06K 9/0053
USPC .......................... 600/481, 483, 485, 490–507
See application file for complete search history.

(56) References Cited

U.S. PATENT DOCUMENTS

| 5,241,964 A | * | 9/1993 | McQuilkin | ................... 600/485 |
| 5,265,011 A | | 11/1993 | O'Rourke | |
| 5,913,826 A | | 6/1999 | Blank | |

(Continued)

FOREIGN PATENT DOCUMENTS

| EP | 1327415 A1 | 7/2003 |
| GB | 2356251 A | 5/2001 |

(Continued)

OTHER PUBLICATIONS

Physical Basis of Pressure Transfer from Periphery to Aorta: A Model-Based Study, AJP—Heart 274: 1386-1392, 1998.

*Primary Examiner* — Navin Natnithithadha
(74) *Attorney, Agent, or Firm* — Karl F. Milde, Jr.; Eckert Seamans Cherin & Mellott, LLC

(57) ABSTRACT

A central arterial blood pressure waveform is developed from pressure waveforms obtained from proximal and distal blood pressure cuffs on the brachial artery of an arm that are inflated to a supra-systolic pressure, The proximal and distal cuff pressure waveforms associated with at least one cardiac ejection cycle are sensed, The propagation times of a blood pressure pulse from the entry of the artery to the proximal cuff and from the proximal cuff to the distal cuff are calculated, permitting calculation of a reflection coefficient of the pressure pulse at one of the proximal and distal cuffs. Assuming a physical model of wave propagation along the artery between the aorta and the proximal and distal cuffs, an estimated pressure waveform at the opening of the artery can be determined.

13 Claims, 27 Drawing Sheets

Overall Flow Diagram of Invention

(56) References Cited

U.S. PATENT DOCUMENTS

| | | | |
|---|---|---|---|
| 6,027,453 A * | 2/2000 | Miwa et al. | 600/485 |
| 6,027,455 A * | 2/2000 | Inukai et al. | 600/490 |
| 6,036,651 A * | 3/2000 | Inukai et al. | 600/485 |
| 6,036,652 A * | 3/2000 | Inukai et al. | 600/493 |
| 6,428,482 B1 | 8/2002 | Sunagawa et al. | |
| 6,511,436 B1 * | 1/2003 | Asmar | 600/500 |
| 6,527,725 B1 * | 3/2003 | Inukai et al. | 600/485 |
| 6,712,768 B2 | 3/2004 | Ogura et al. | |
| 6,740,045 B2 | 5/2004 | Amano | |
| 6,746,405 B2 | 6/2004 | Narimatsu | |
| 6,786,872 B2 | 9/2004 | Narimatsu et al. | |
| 6,793,628 B2 | 9/2004 | Ogura et al. | |
| 6,802,814 B2 | 10/2004 | Narimatsu | |
| 6,808,496 B2 | 10/2004 | Oka et al. | |
| 6,814,705 B2 | 11/2004 | Kawaguchi | |
| 6,976,966 B2 | 12/2005 | Narimatsu | |
| 7,326,180 B2 | 2/2008 | Tanabe et al. | |
| 7,468,037 B2 | 12/2008 | Illyes et al. | |
| 7,621,876 B2 * | 11/2009 | Hoctor et al. | 600/504 |
| 7,674,231 B2 * | 3/2010 | McCombie et al. | 600/485 |
| 8,313,439 B2 * | 11/2012 | Mccombie et al. | 600/485 |
| 8,517,951 B2 * | 8/2013 | Fujii et al. | 600/490 |
| 2004/0077959 A1 | 4/2004 | Narimatsu | |
| 2006/0167359 A1 * | 7/2006 | Bennett et al. | 600/485 |
| 2006/0195034 A1 | 8/2006 | Skrabal et al. | |
| 2008/0064967 A1 * | 3/2008 | Ide | 600/490 |
| 2008/0066753 A1 * | 3/2008 | Martin et al. | 128/204.23 |

FOREIGN PATENT DOCUMENTS

| | | |
|---|---|---|
| WO | 9011043 A1 | 10/1990 |
| WO | 2006106439 A2 | 10/2006 |
| WO | 2008025053 A1 | 3/2008 |
| WO | 2008121454 A1 | 10/2008 |

* cited by examiner

Fig 1: Device Block Diagram

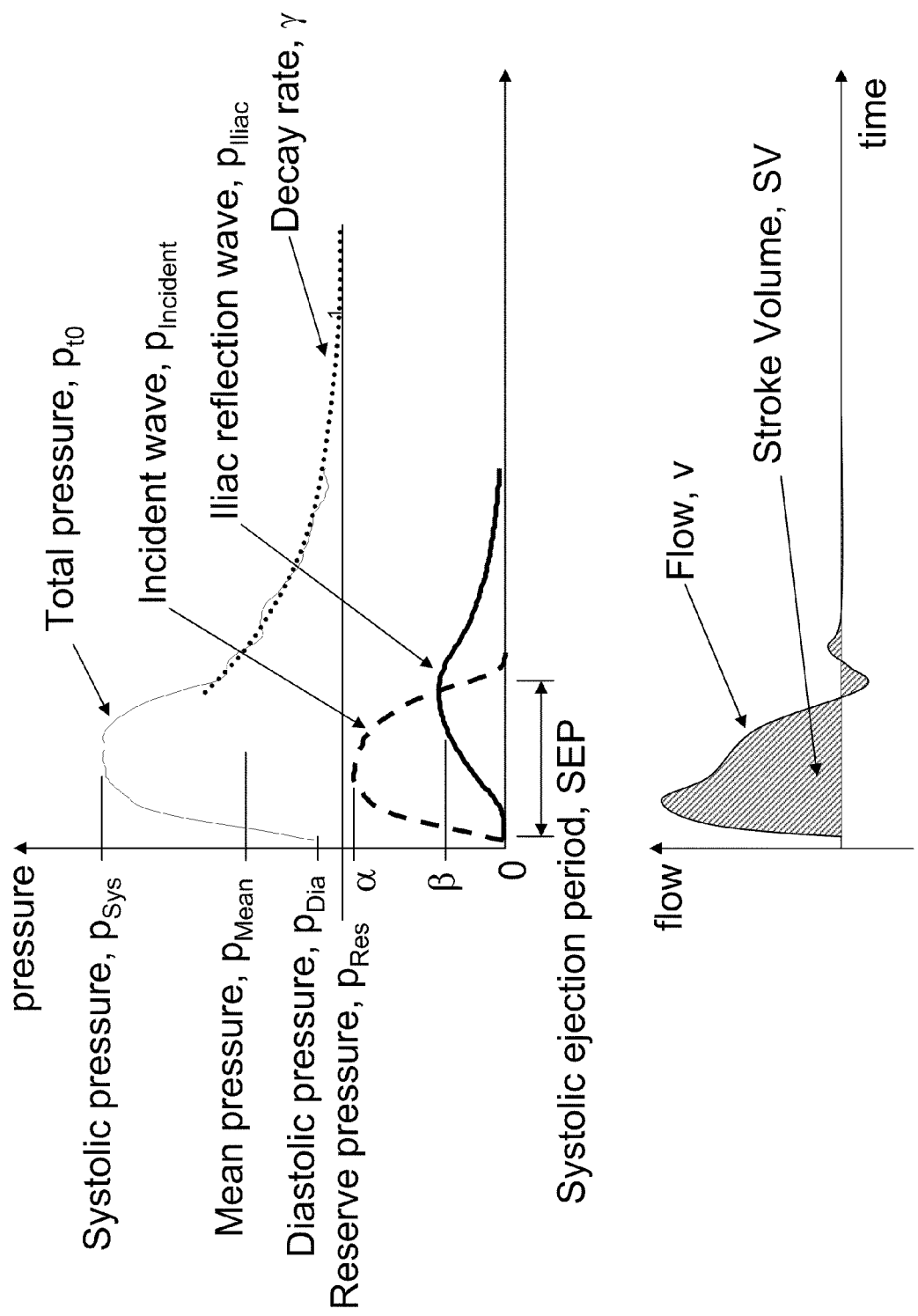
Fig 3. Medical parameters

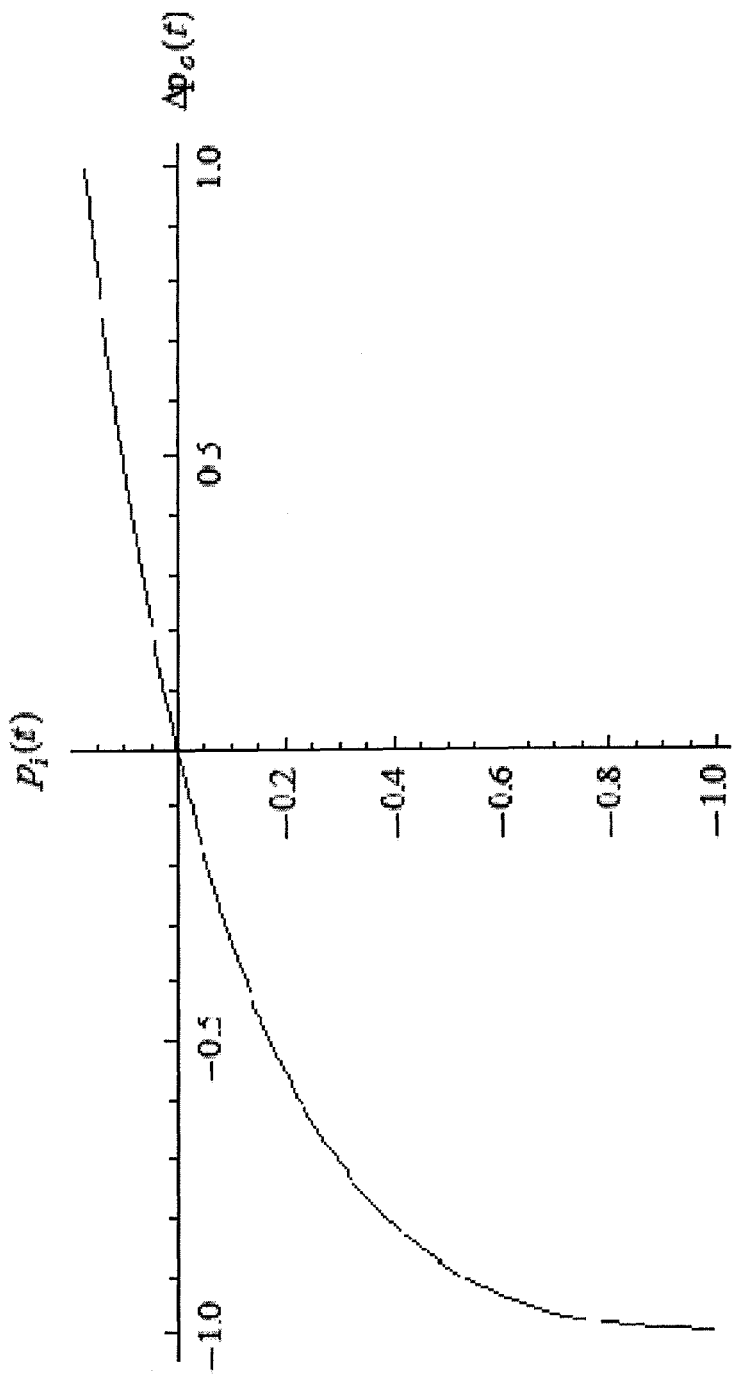
Fig 4: Normalised relationship between cuff oscillation and intra-arterial pressure

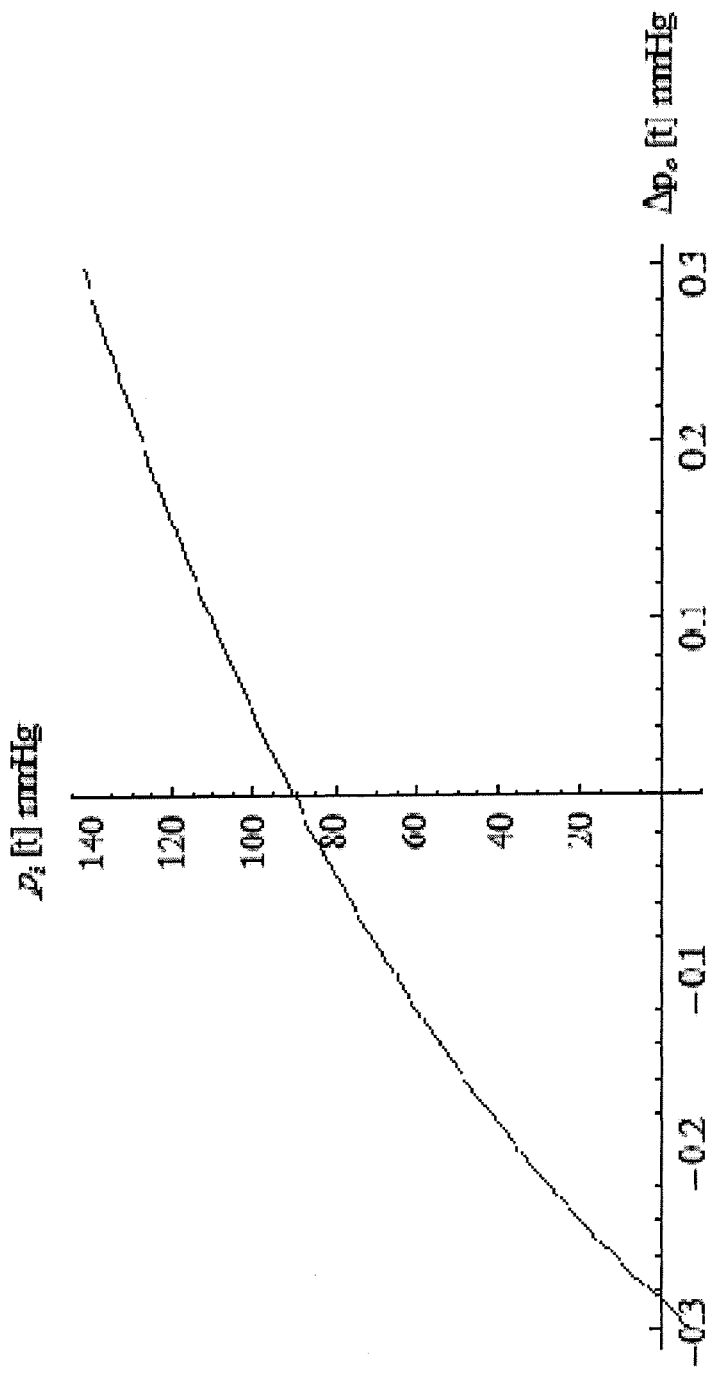
Fig 5: Relationship between cuff oscillation and intra-arterial pressure at physiological scales

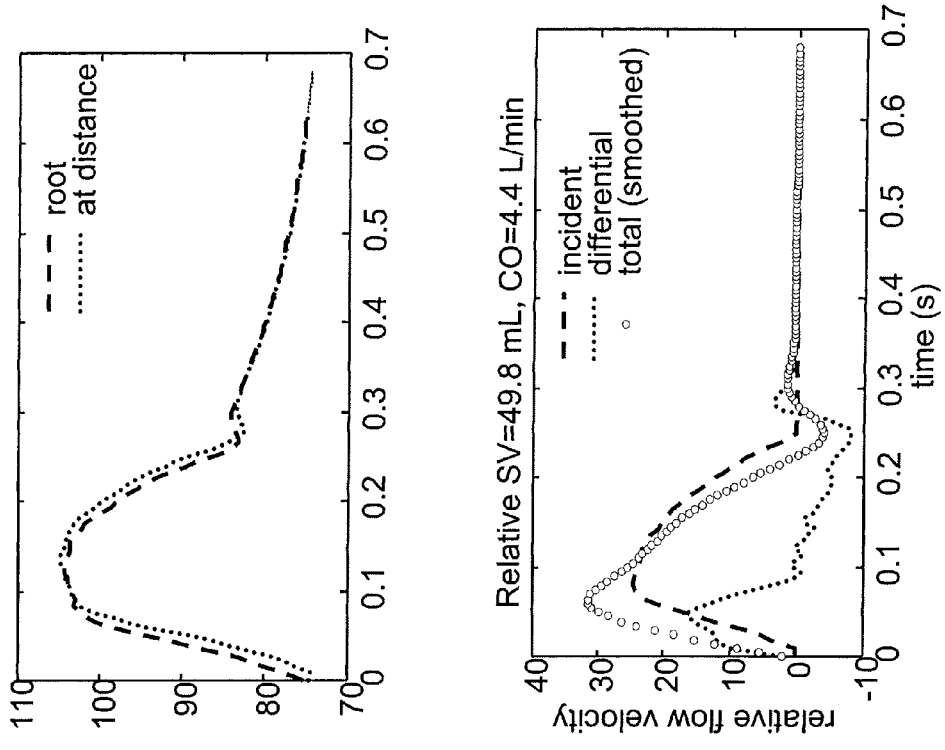
Fig 6: Phenylephrine, Baseline

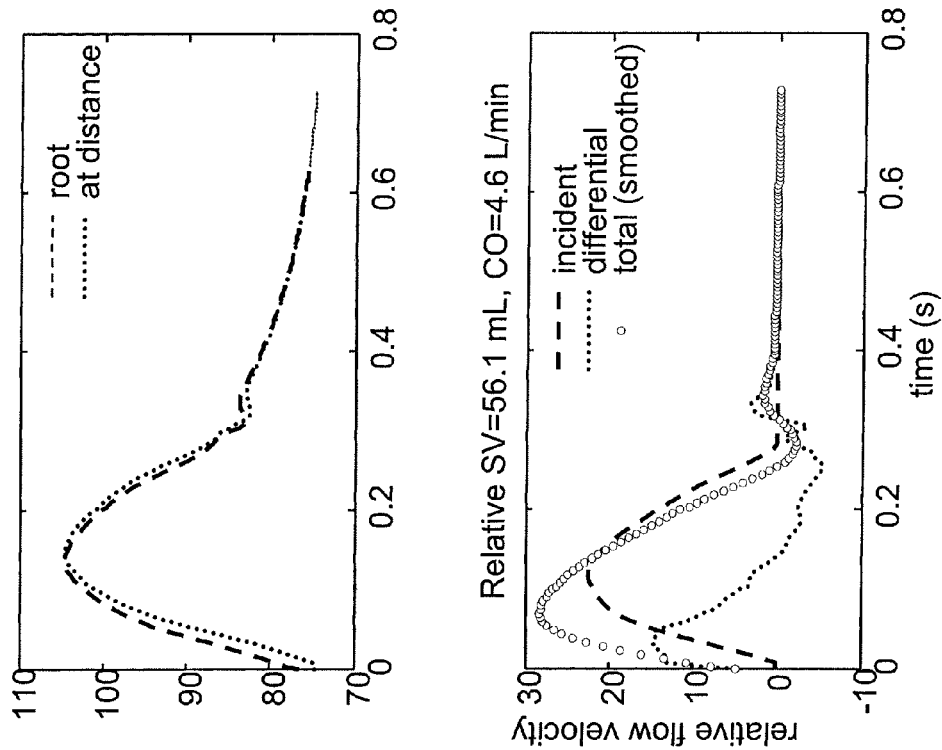
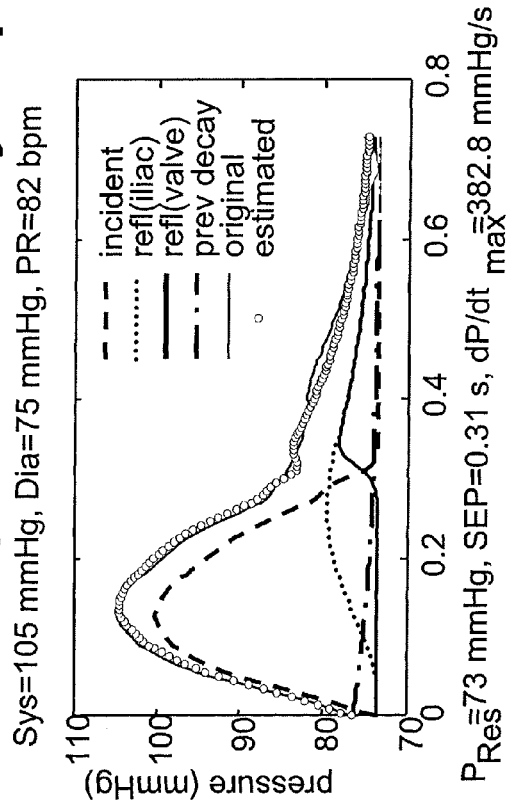
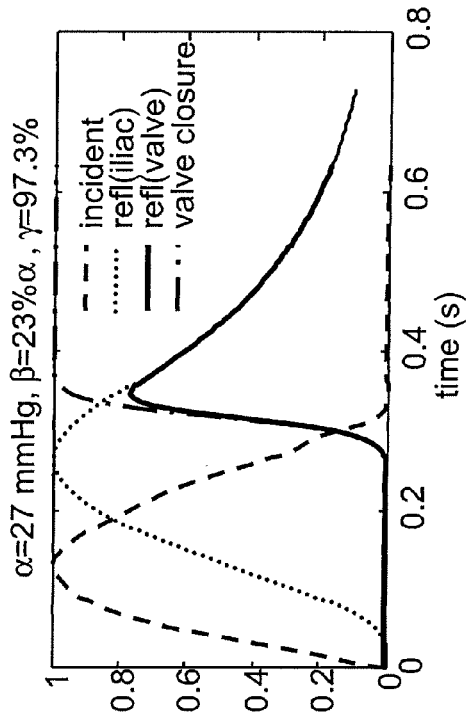
Fig 7, Phenylephrine, Induction

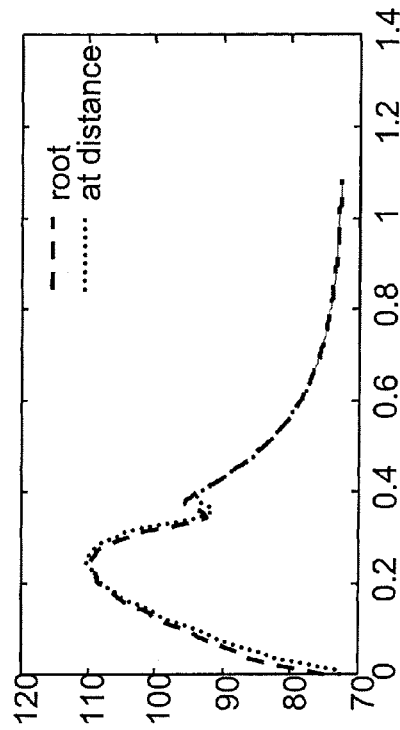
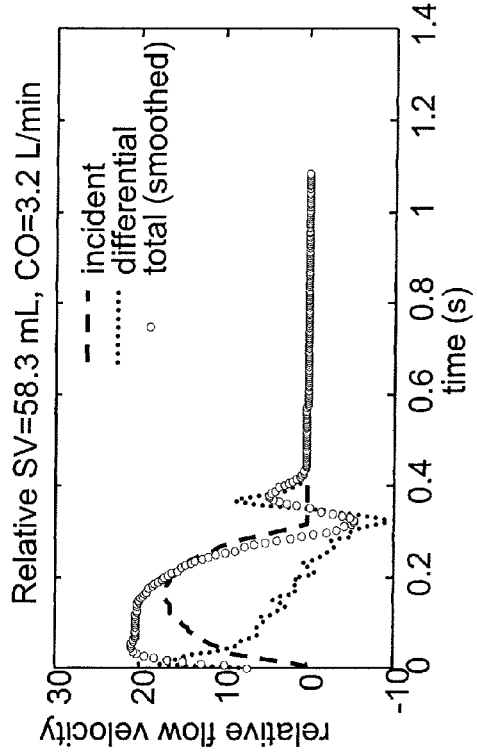
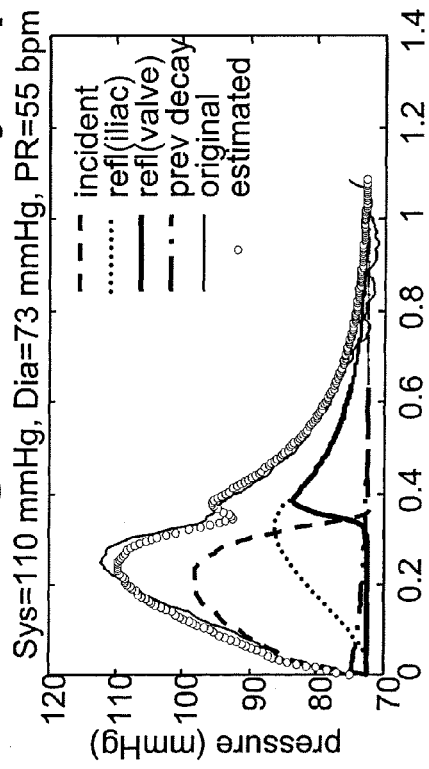
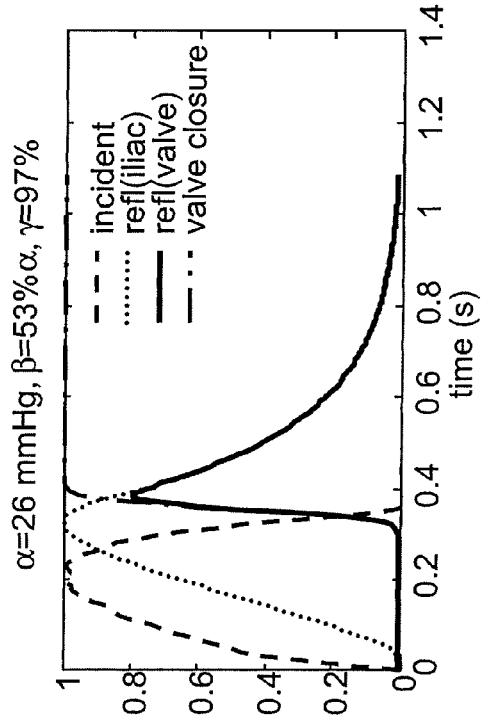
Fig 8: Phenylephrine, Post Tq Up

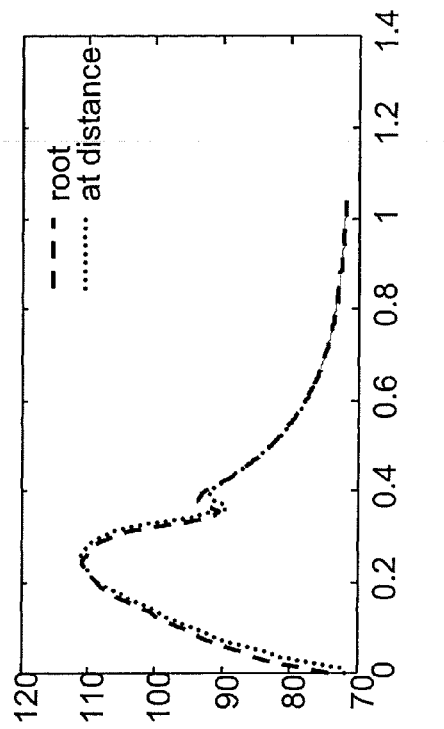
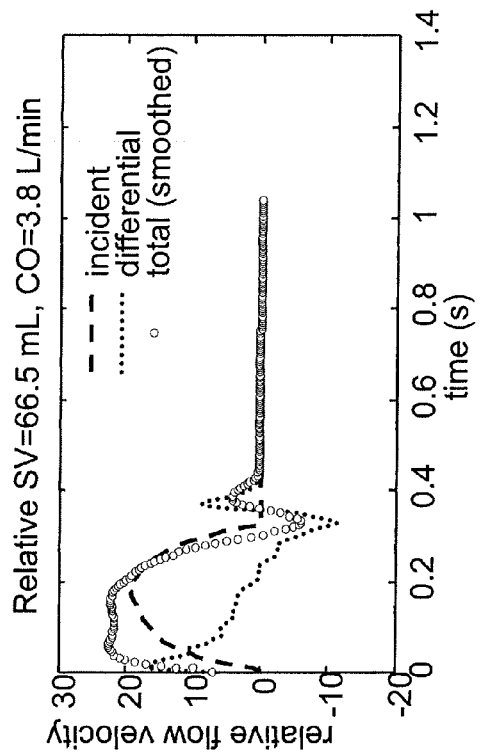
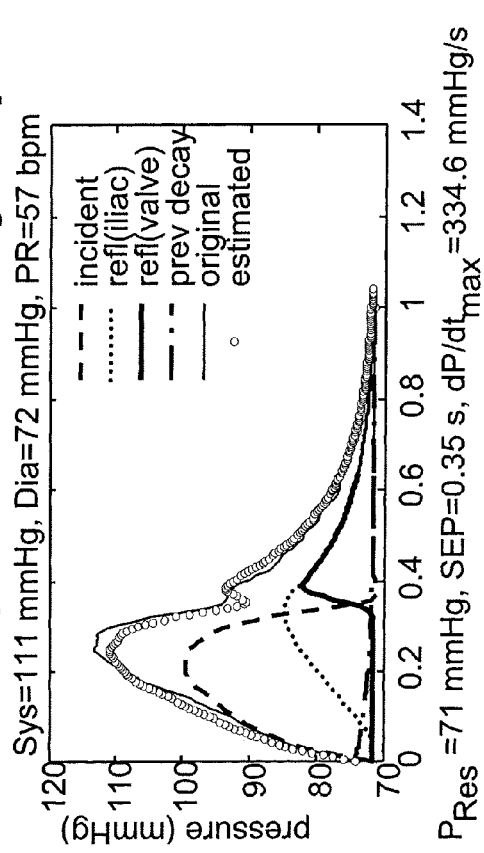
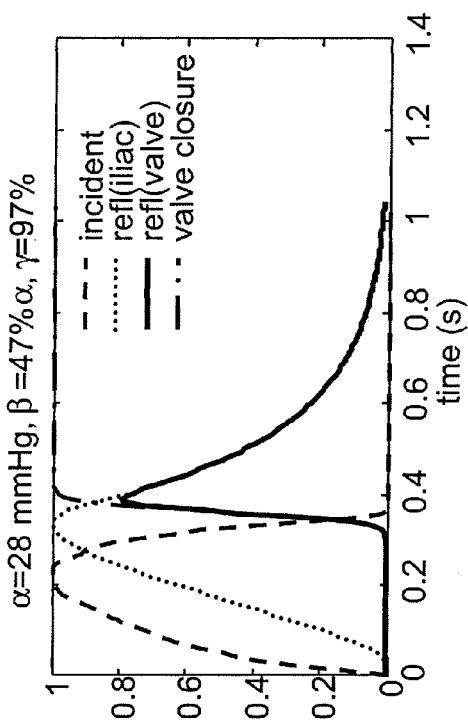
Fig 9: Phenylephrine, Pre Tq Dn

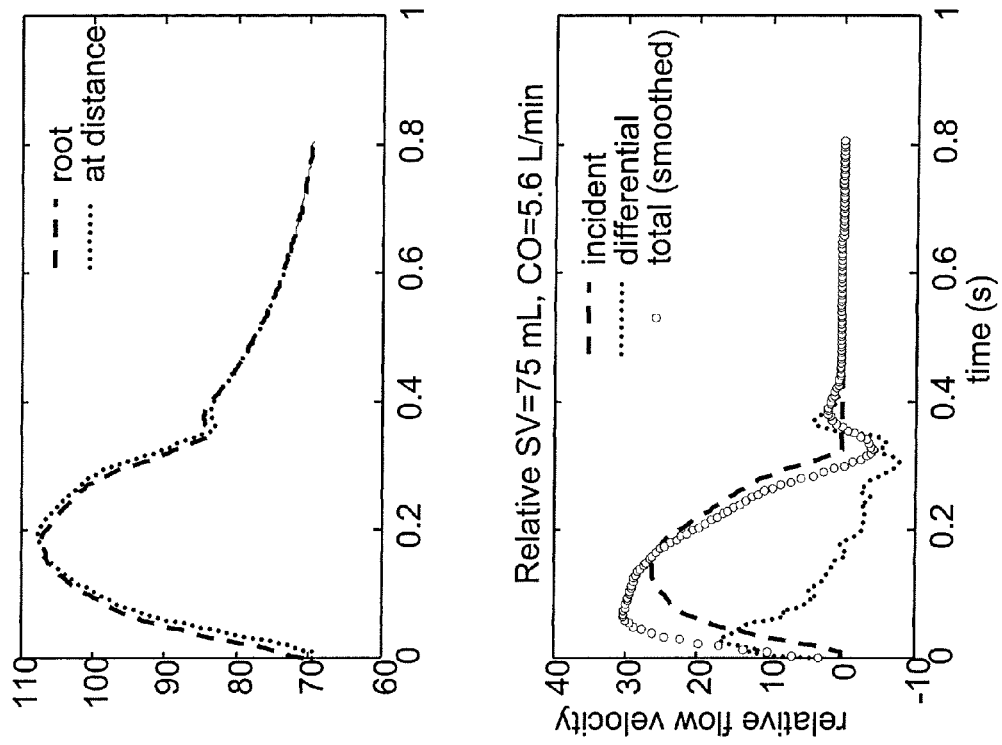
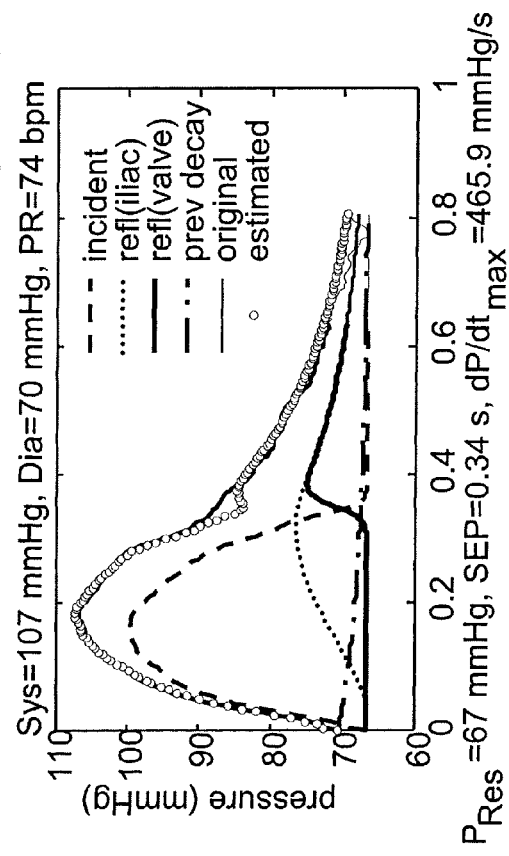
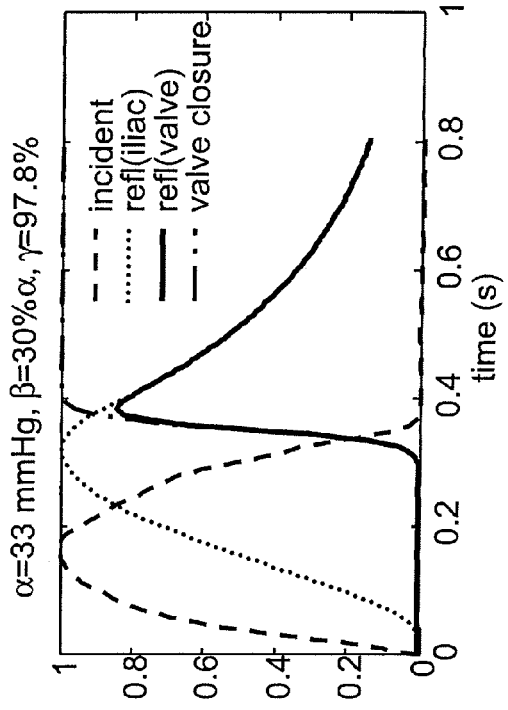
Fig 10: Phenylephrine, Post Tq Dn

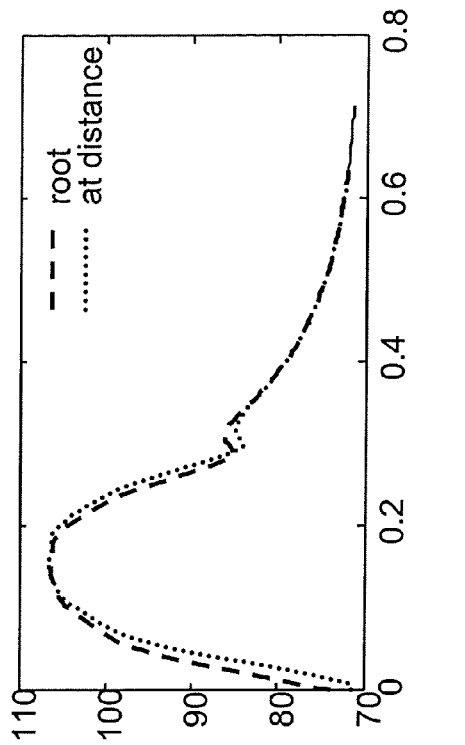
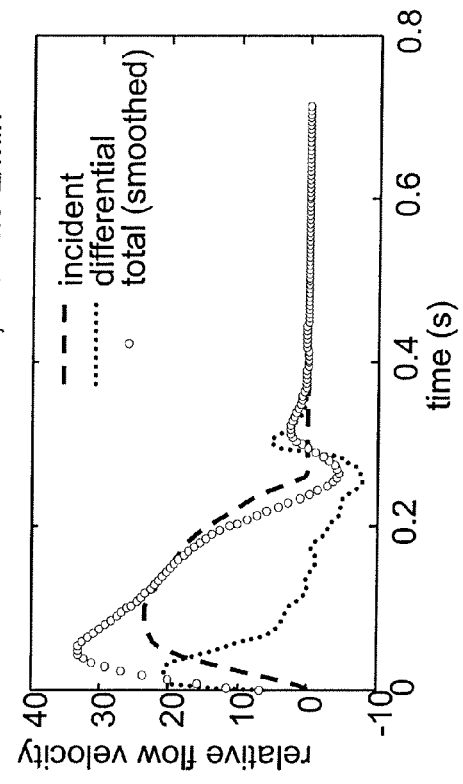
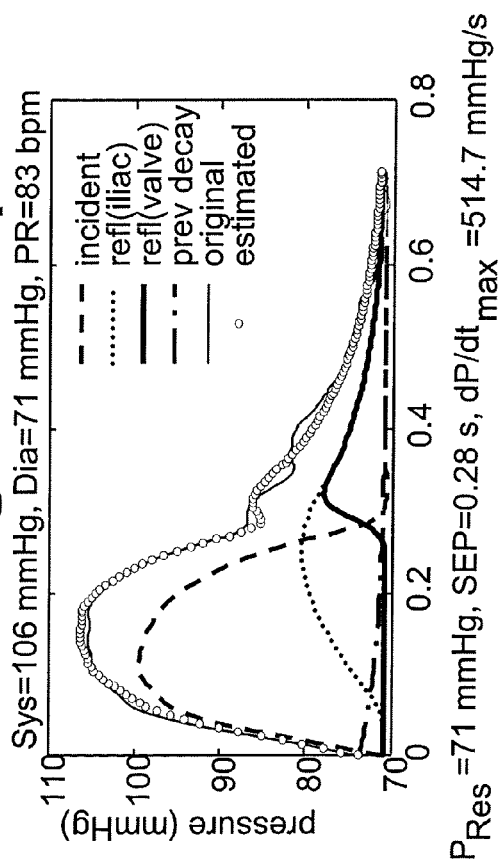
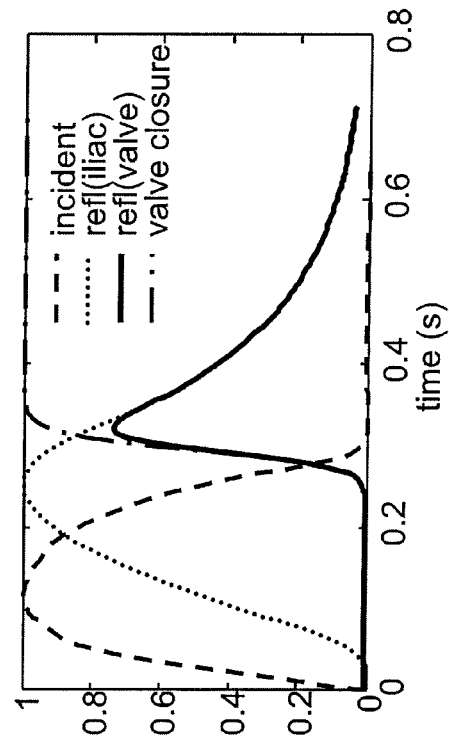
Fig 11: Ephedrine, Baseline

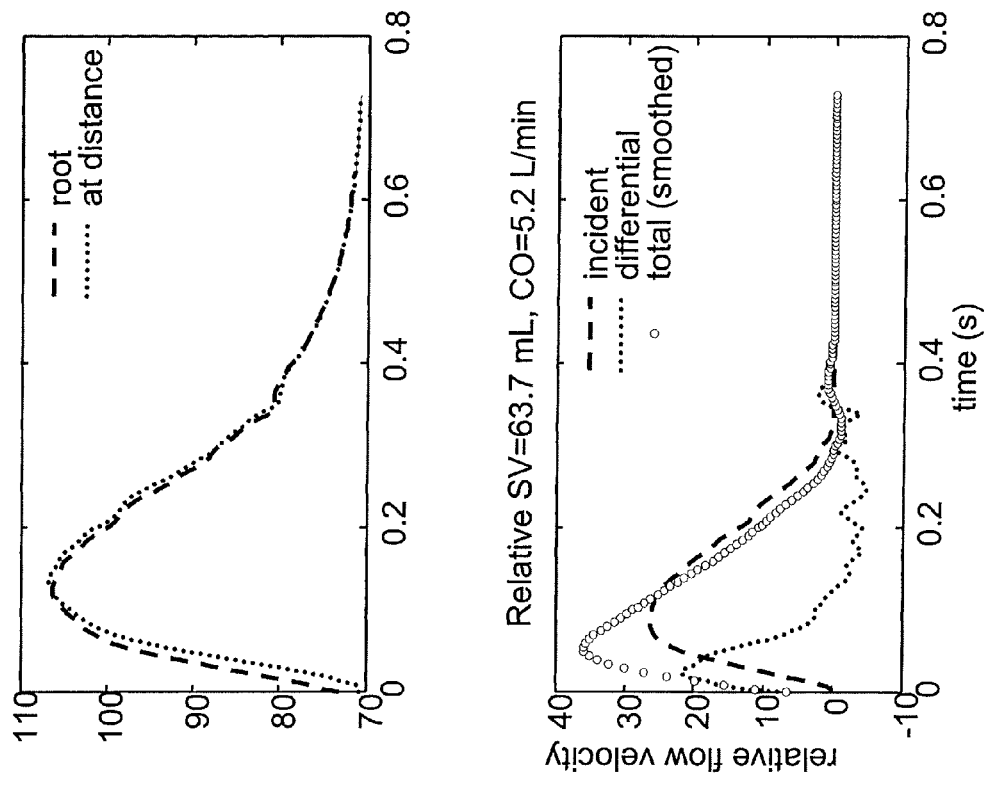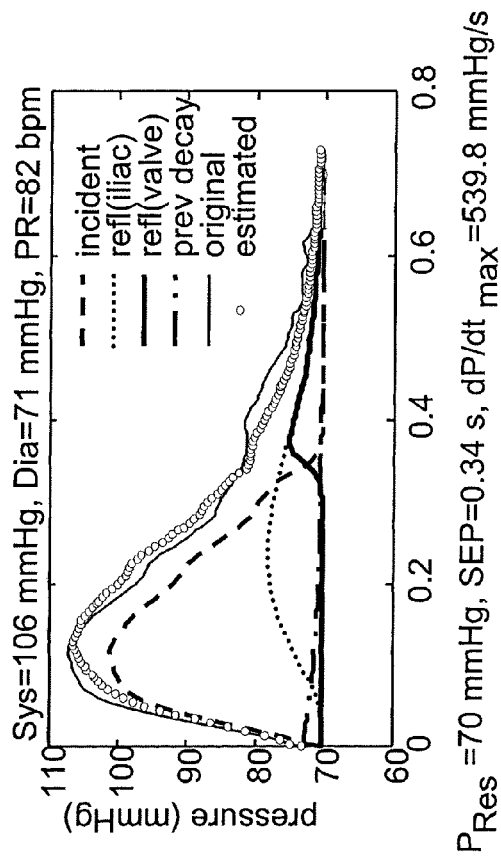
Fig 12: Ephedrine, Induction

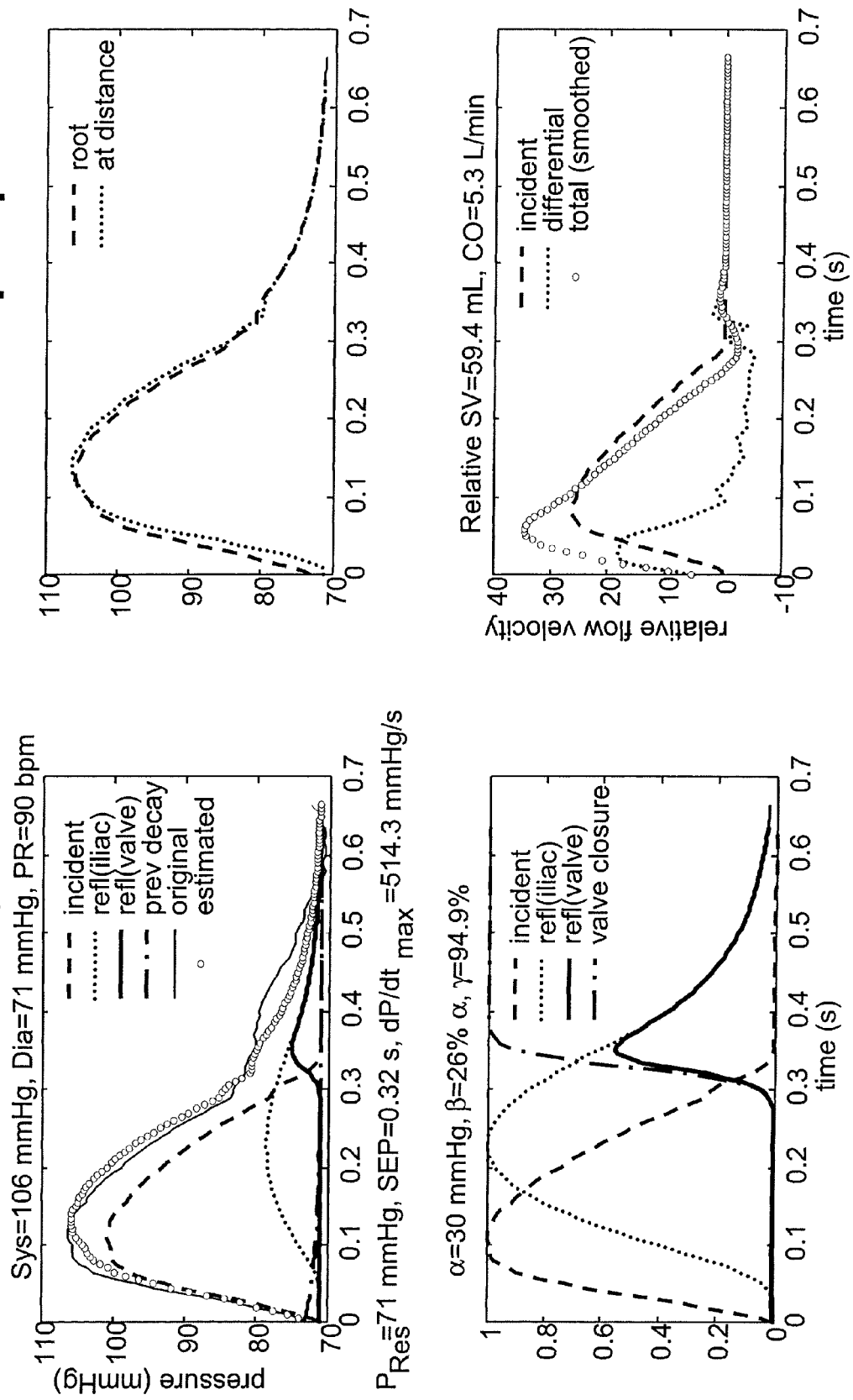

Fig 14: Ephedrine, Pre Tq Dn
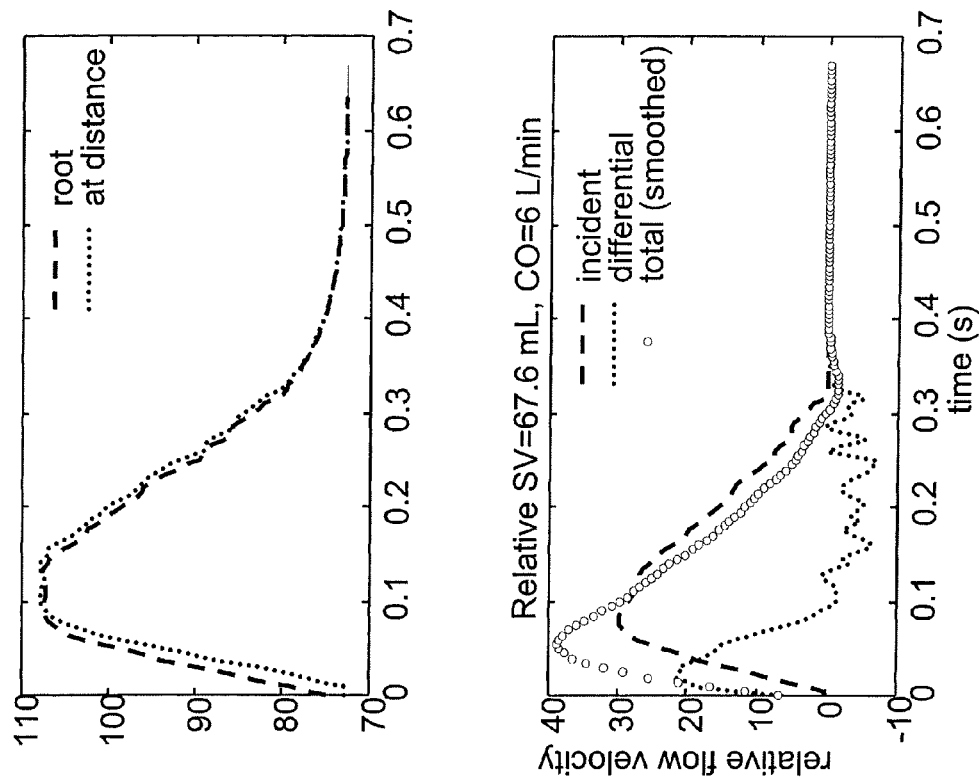
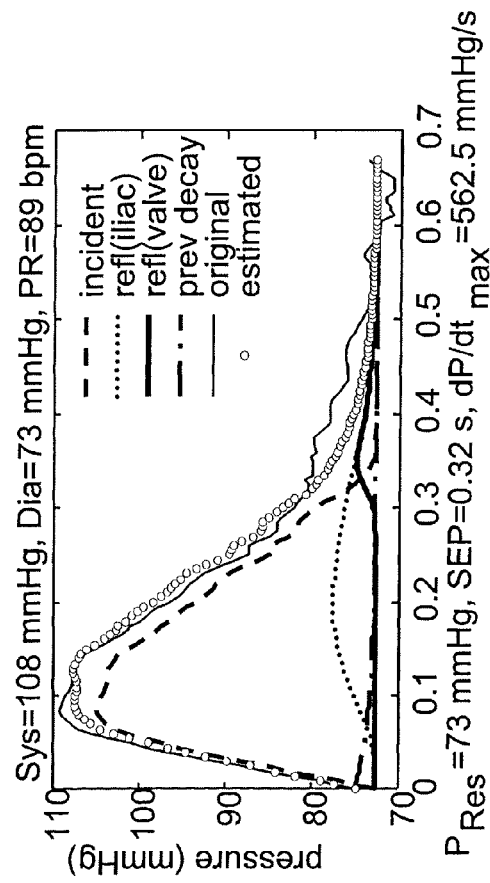
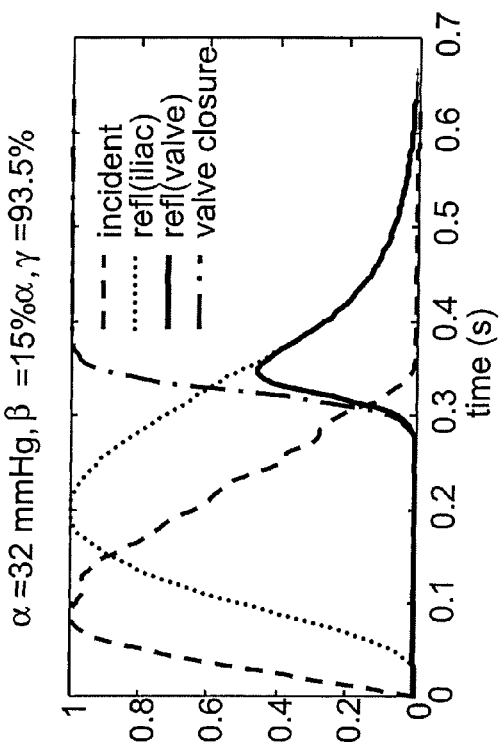

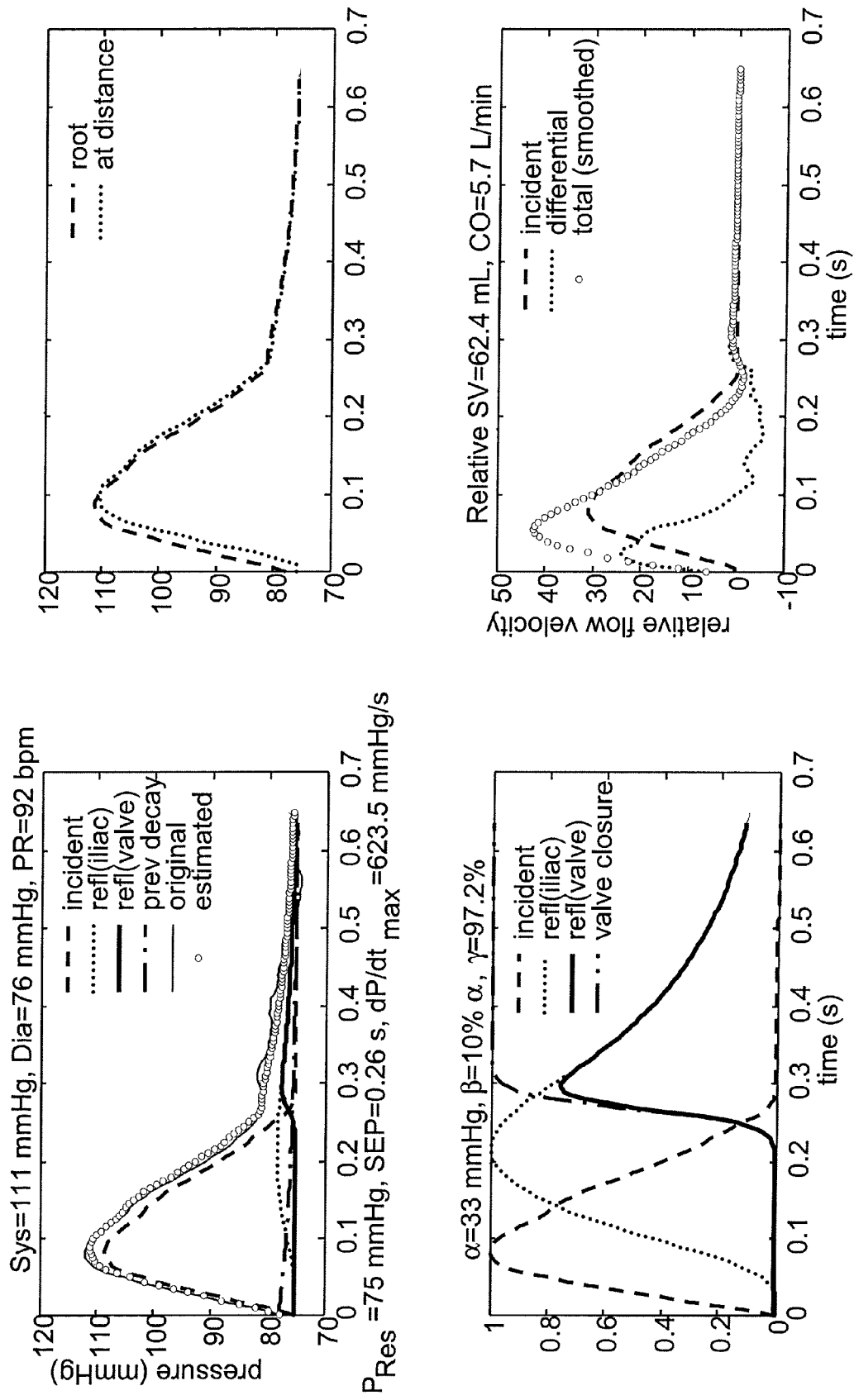
Fig 15: Ephedrine, Post Tq Dn

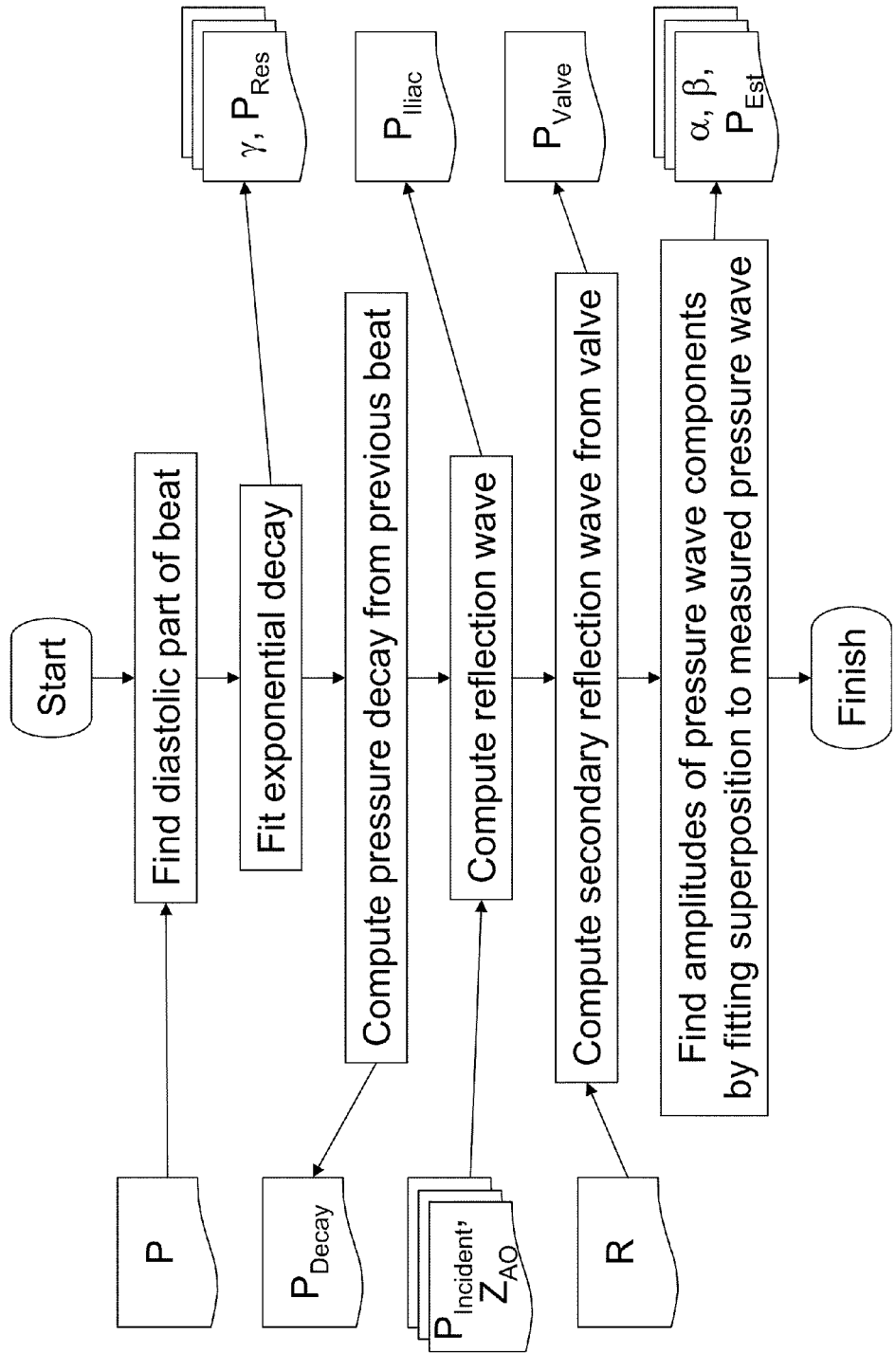
Fig 16. Decomposition of Central Pressure Waveform

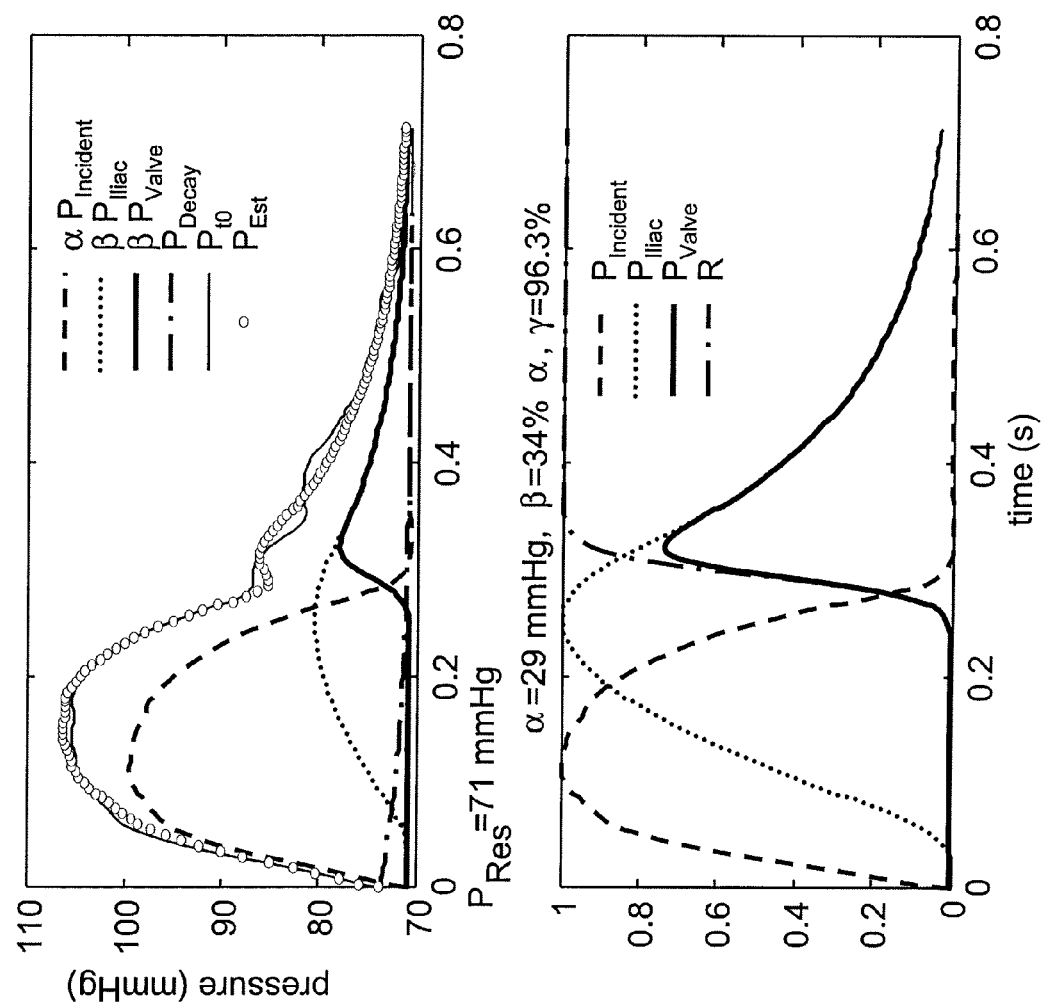
Fig 17. Illustration of decomposition

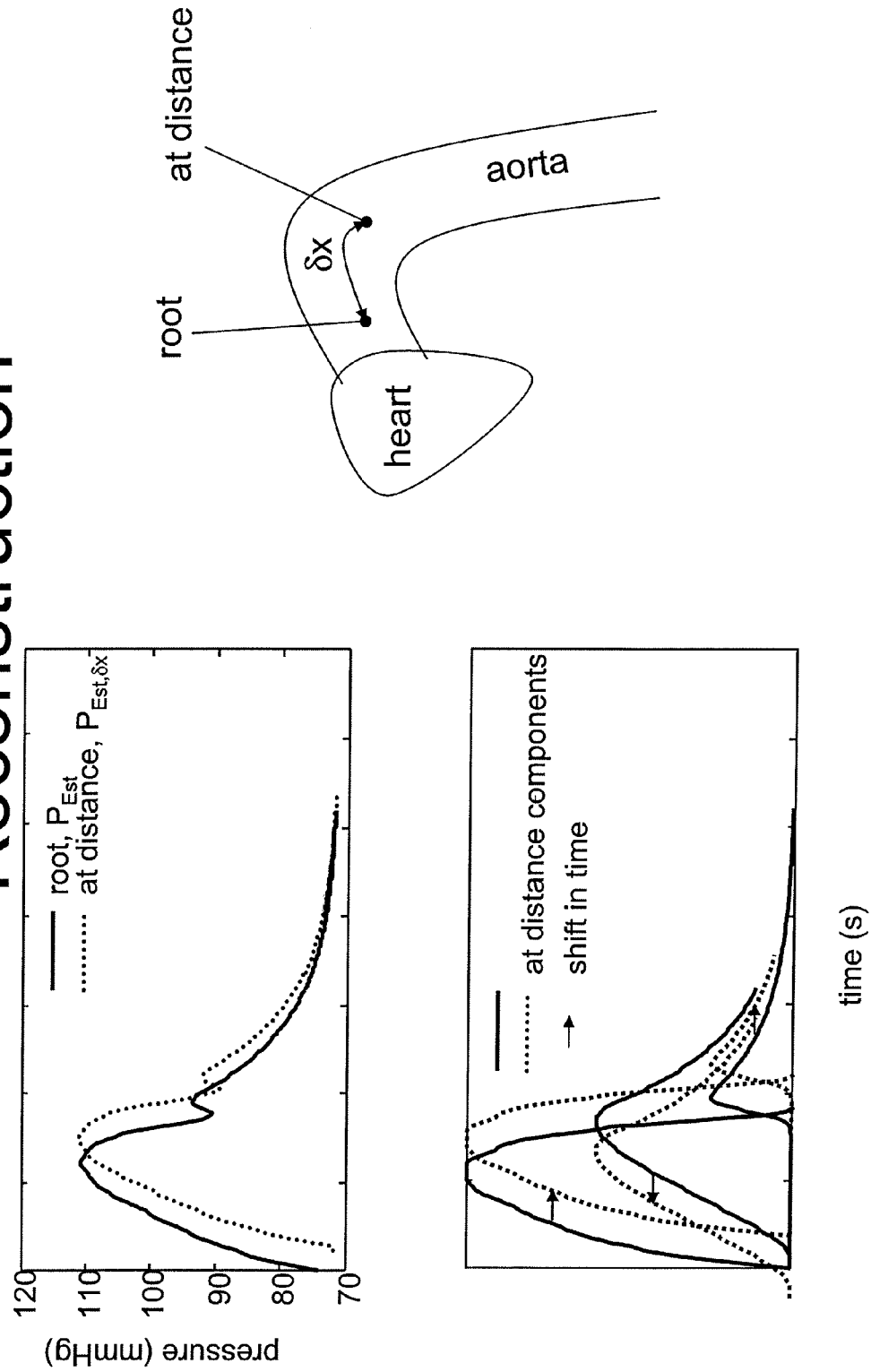
Fig 18. Illustration of Downstream Reconstruction

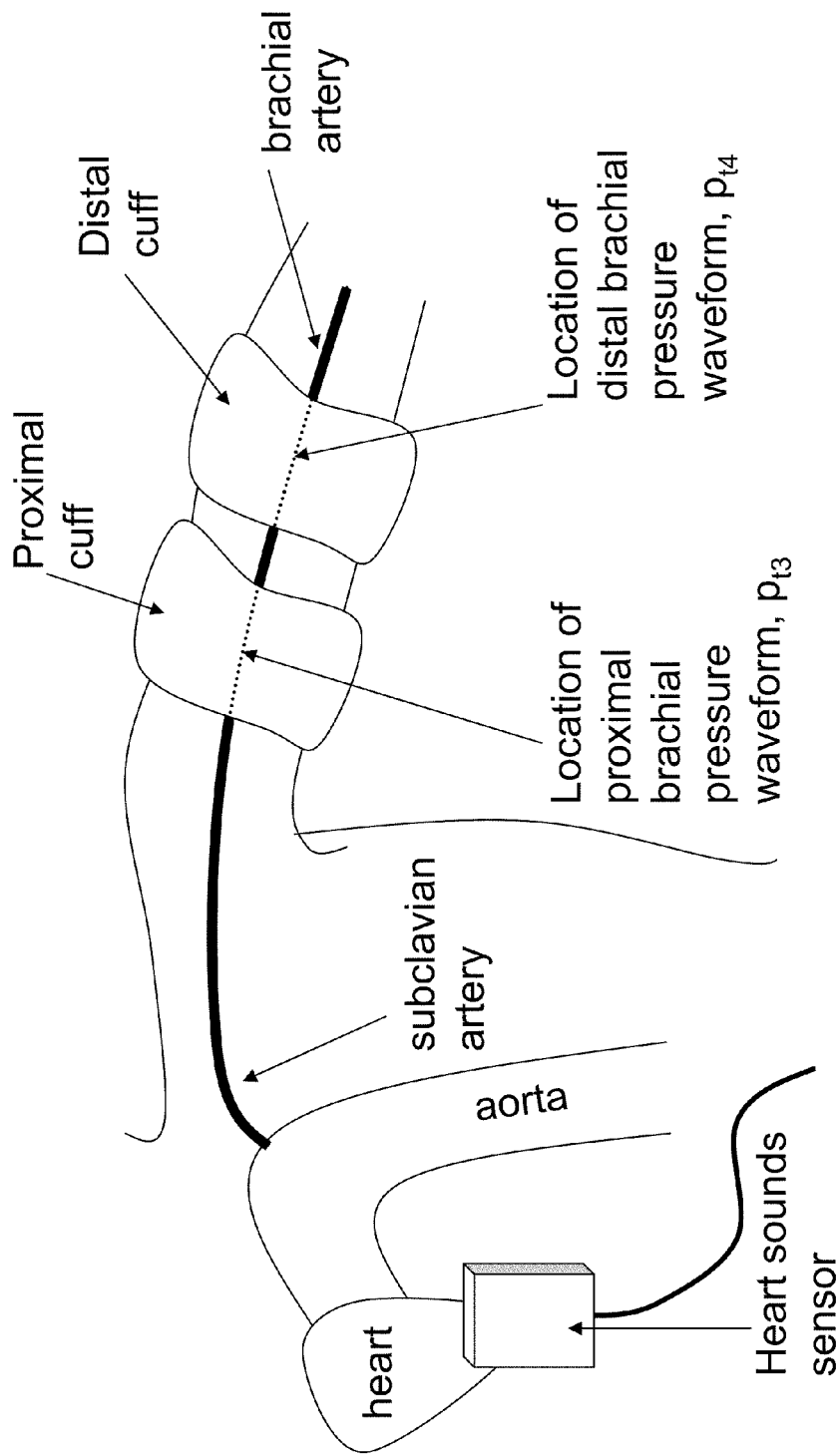
Fig 19. Proximal and distal cuffs

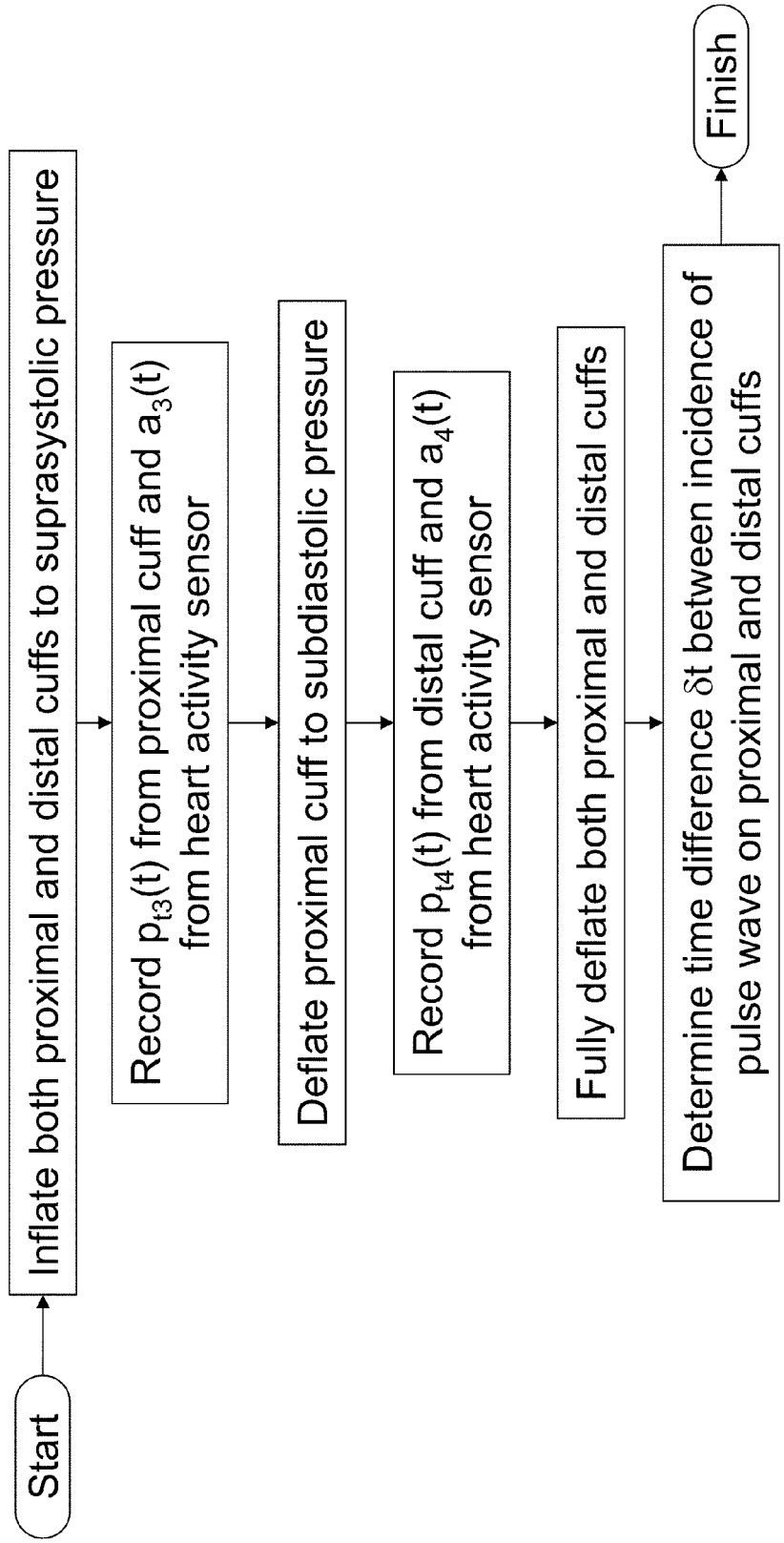
Fig 20: Use of proximal and distal cuffs

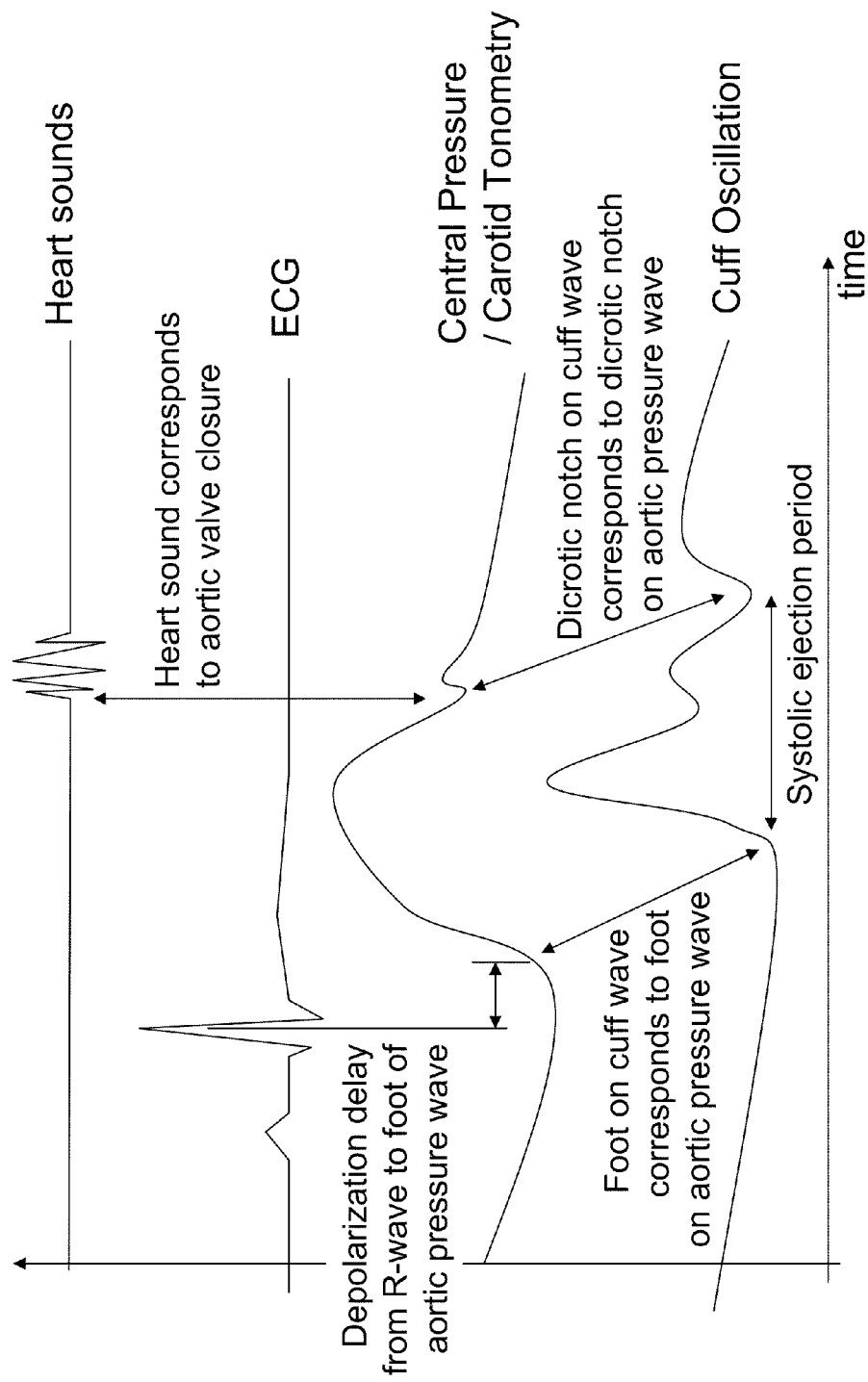

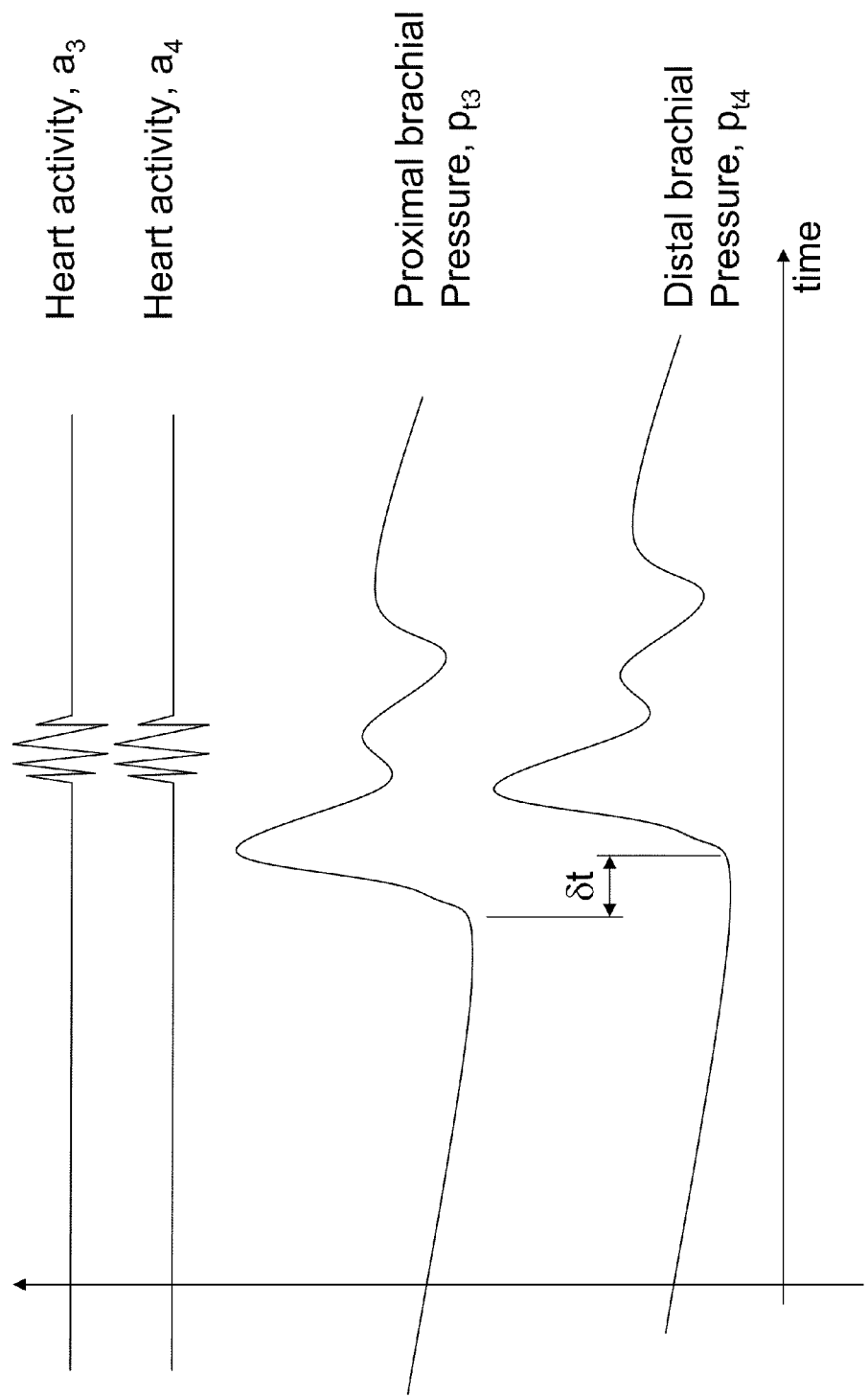
Fig 22: Estimation of Propagation Time from Proximal to Distal Cuff

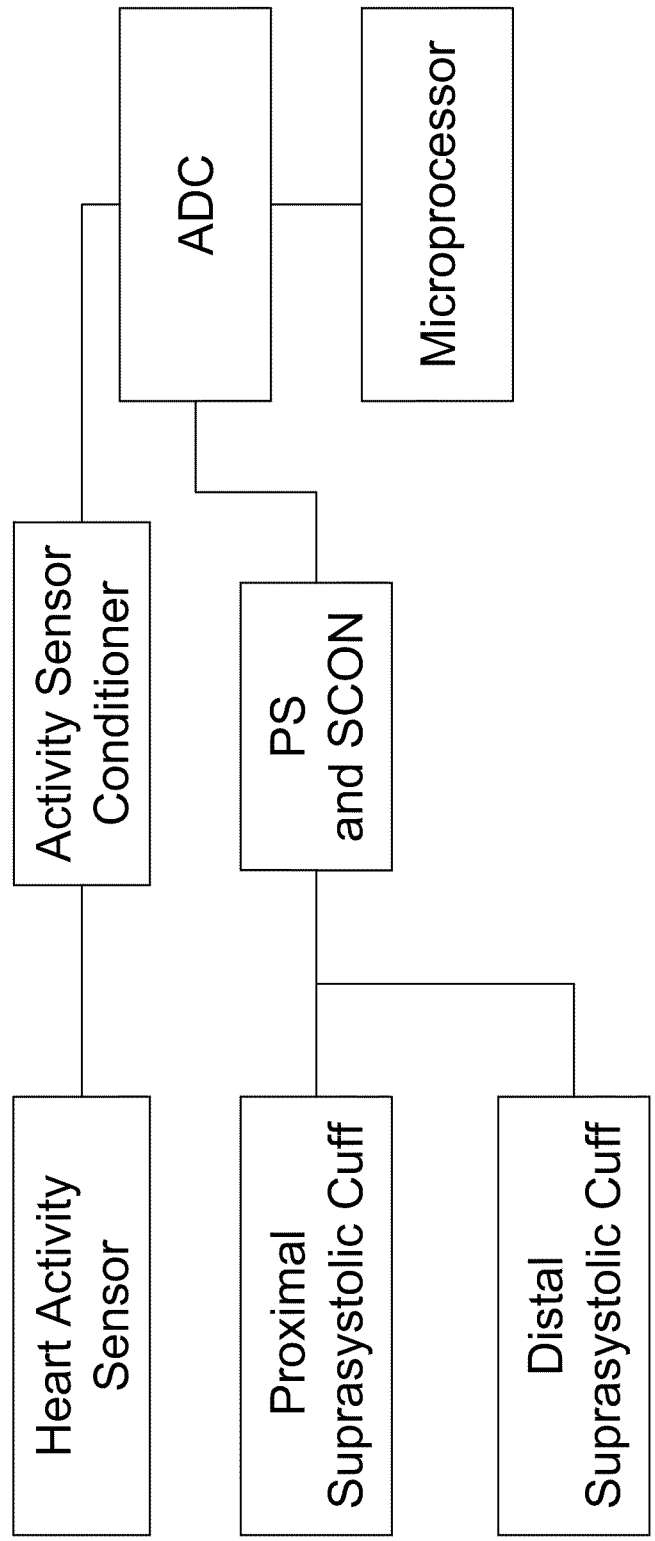
Fig 23: Pulse Propagation Model Estimation Apparatus

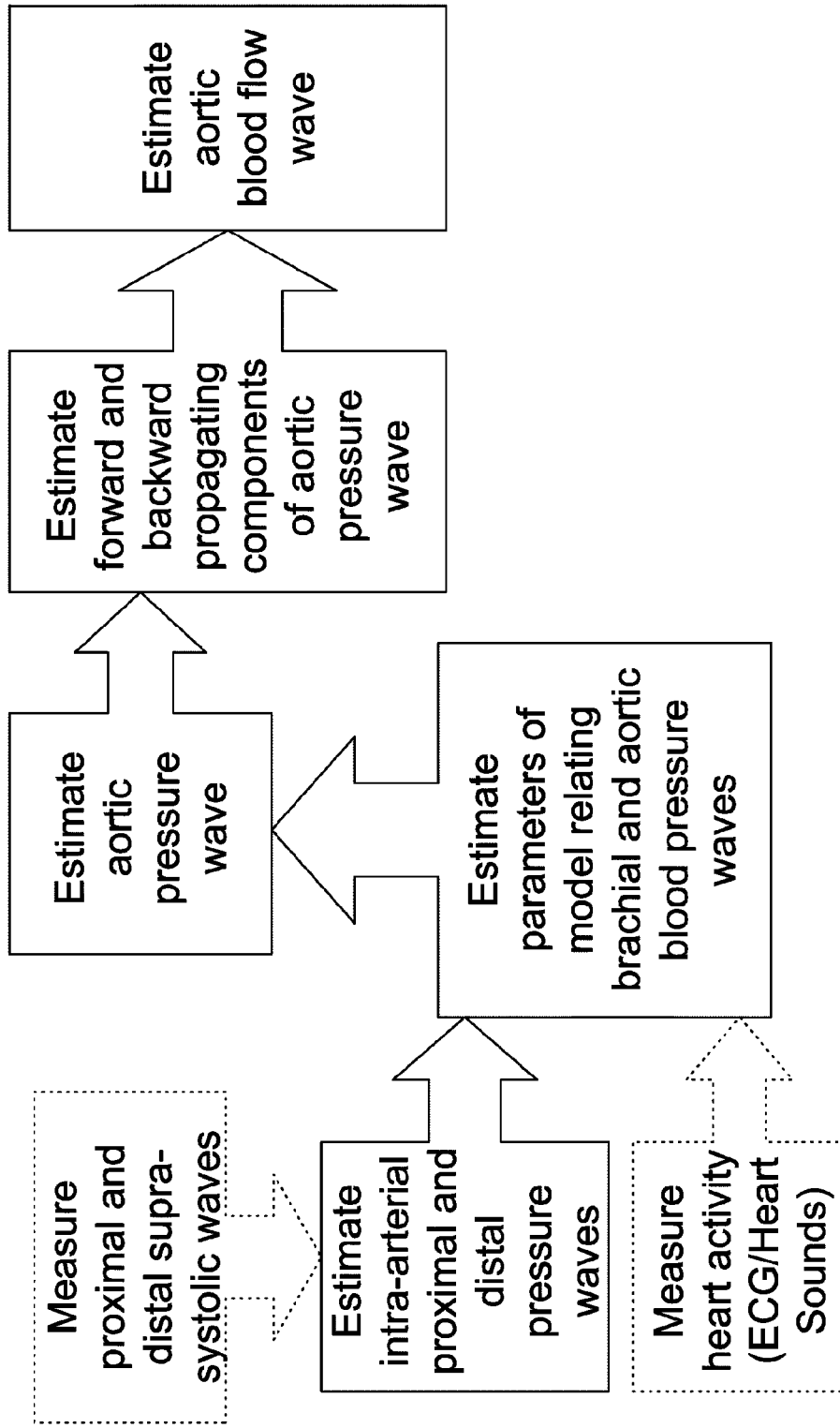

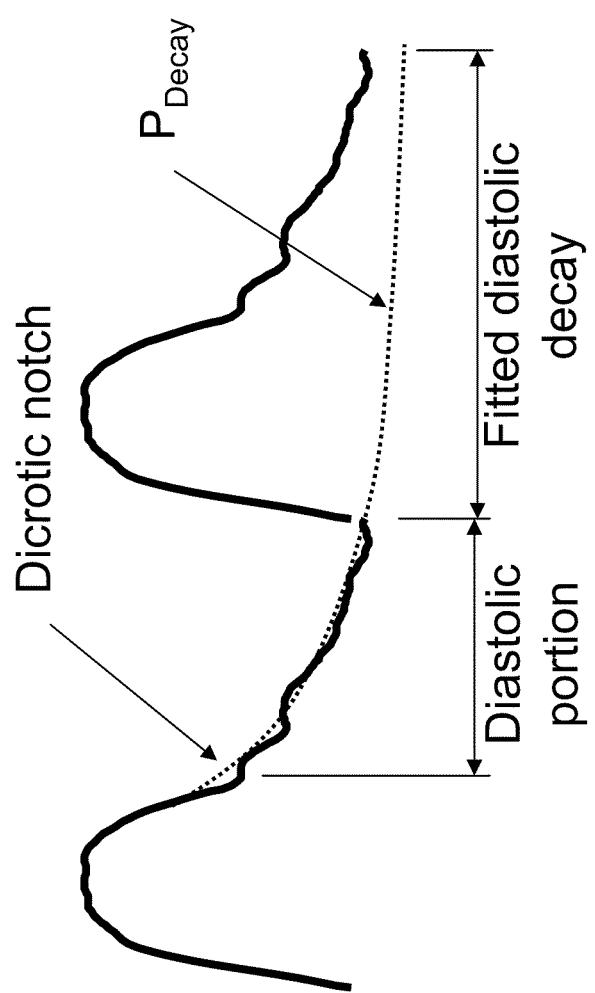
Fig 25: Fitted exponential decay

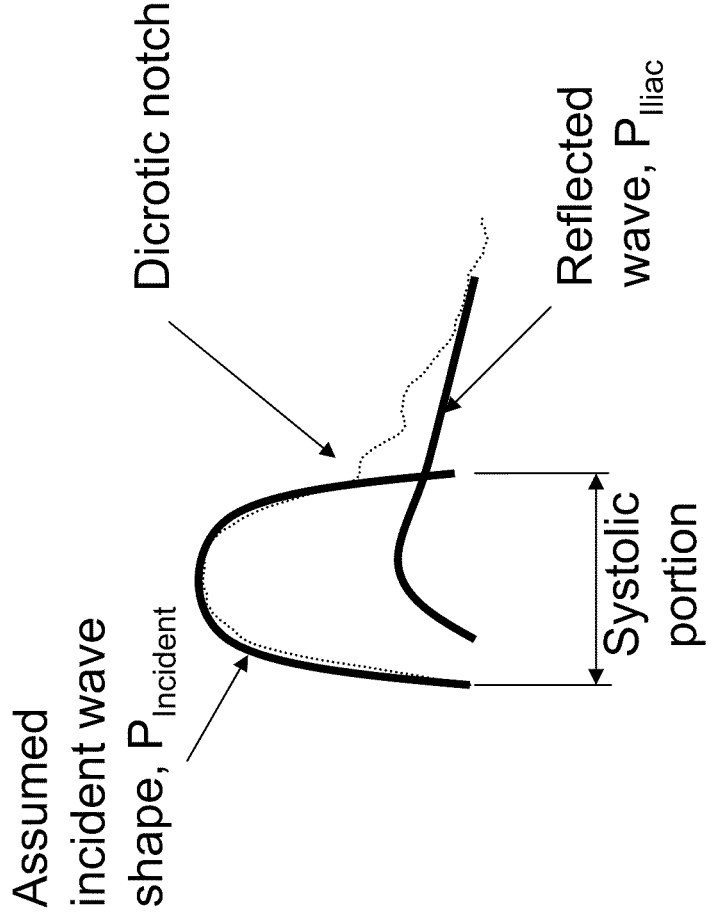
Fig 26: Incident and reflected wave

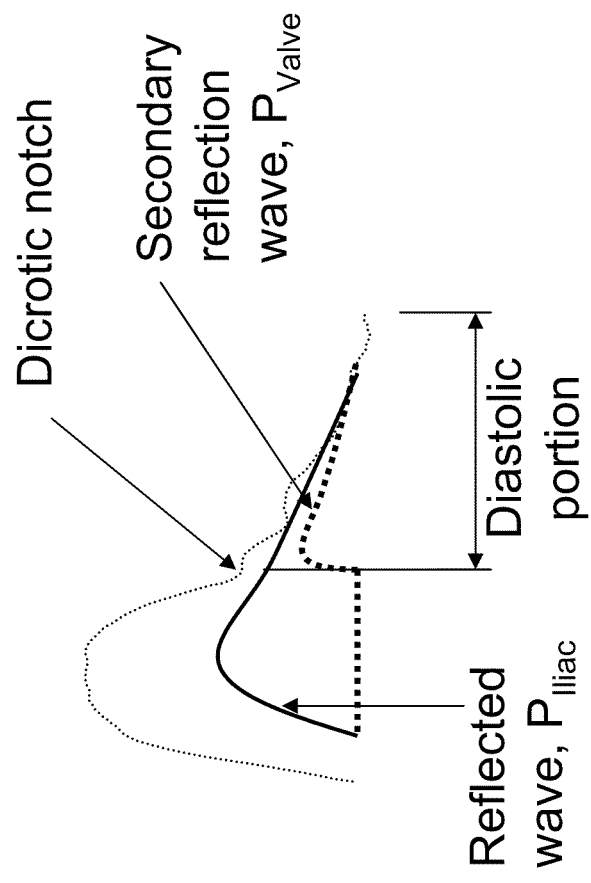
Fig 27: Valve reflection wave

METHOD AND APPARATUS FOR PRODUCING A CENTRAL PRESSURE WAVEFORM IN AN OSCILLOMETRIC BLOOD PRESSURE SYSTEM

CROSS-REFERENCE TO RELATED APPLICATIONS

This present application is a continuation-in-part of U.S. patent application Ser. No. 12/455,516, filed Jun. 3, 2009; U.S. patent application Ser. No. 11/358,283, filed Feb. 21, 2006 (now U.S. Patent Publication No. 2006/0224070-A1, published Oct. 5, 2006, and now abandoned); U.S. patent application Ser. No. 12/157,854, filed Jun. 13, 2008 (now U.S. Patent Publication No. 2009/0012411-A1, published Jan. 8, 2009) and claims priority from U.S. Provisional Application Ser. No. 61/201,540, filed Dec. 11, 2008. The invention disclosed and claimed herein is related in subject matter to that disclosed in U.S. Pat. No. 5,913,826, issued Jun. 22, 1999; U.S. Pat. No. 6,994,675, issued Feb. 7, 2006; and the aforementioned U.S. Patent Publication No. 2006/0224070-A1 and U.S. Patent Publication No. 2009/0012411-A1, all of which are incorporated herein by reference.

BACKGROUND OF THE INVENTION

Blood pressure is the net result of stroke volume and vascular resistance or impedance. Blood pressure can increase with an increase in stroke volume as occurs with exercise or with adrenaline. Blood pressure can also increase with an increase in arterial tone, which is the usual cause of essential hypertension. Blood pressure increases with vasoconstrictors such as phenylephrine or angiotensin which raise blood pressure solely by increasing vascular stiffness.

It would be very useful to be able to quantify the relative contribution of stroke volume and arterial stiffness to blood pressure. For example, if the oscillometrically measured blood pressure is 150/80, are these high numbers due to increases in stroke volume or from arterial stiffness? The decision to treat or not to treat, and/or the determination of what agent to use, could vary, depending upon the result.

Similarly, the response to the treatment to be followed can vary with the result. For example, if a vasodilator such as an angiotensin receptor blocker (ARB) is used, the change in vascular stiffness may be more important to follow, rather than blood pressure alone, as arterial stiffness is the primary pathology.

In the acute care setting, a non-invasive measure would help in decision-making to diagnose and manage heart failure or sepsis with vasoactive drugs and fluid.

There is also a large group of people with normal blood pressure but increased vascular stiffness. A non-invasive way of assessing the degree of vasoconstriction and cardiac performance would be helpful in diagnosing and treating such patients. Other patients have unrecognized vascular stiffness yet their blood pressure does not reach the 140/90 threshold of treatment. How to treat (or not to treat) these patients is unclear. The ability to further characterize those patients who may have so-called "pre-hypertension" into those with and without vascular stiffness could provide a way forward in therapy and prevention of premature vascular death.

Increasingly, there is evidence that the central, aortic blood pressure and flow waveforms contain information that can help to answer the questions above. However, the indices commonly derived from the pressure waveform are based on apparent morphology, rather than the underlying physics, there are difficulties in accurately estimating the central pressure waveform morphology from a non-invasive measurement, and it is difficult to measure the aortic flow waveform in a non-invasive manner. This invention addresses all of these issues.

SUMMARY OF THE INVENTION

Estimation of Intra-Arterial Brachial Blood Pressure Waveforms.

The U.S. patent application Ser. No. 12/455,516, filed Jun. 3, 2009. referred to above, discloses the transformation of an oscillometric waveform recorded by a cuff to an estimate of the internal (brachial) arterial waveform. The correction was previously given such that the oscillometric waveform was rescaled between systolic and diastolic pressures, and then a correction amount applied such that the correction amount was zero at zero transmural pressure, and increased by increasing amounts as transmural pressure increases. The correction amount was given as a fourth power of the transmural pressure. The corrected waveform was then rescaled again to between systolic and diastolic pressure.

According to the present invention an alternative scaling method is provided, based on a simplified physics model, allowing better understanding and parameter identification methodologies to be employed, in order to adapt the model to specific subjects.

It is first assumed that the cuff contains a fixed (molar) amount of fluid (usually air) during the measurement (as is the case during suprasystolic oscillometric measurement). Then the bulk modulus, K, relates the change in volume to the change in pressure, assuming there are no dynamic effects:

$$K = -\frac{V(0)(p_o(t) - p_o(0))}{V(t) - V(0)}$$

It is also assumed that the change in volume is completely accounted for by a change in the radius of the inner wall of the cuff, i.e. a change in outer radius of the arm. This equation is a linear approximation of the change in volume, where w is the width of the cuff.)

$$V(t) - V(0) = -2\pi w r_o(t)(r_o(t) - r_o(0))$$

One can model the soft tissue under the cuff as a thick-walled cylinder (see Benham and Crawford, eq 15.18), with the artery at the centre of the cylinder. This assumes there is some "effective" internal and external radius ratio. The actual geometry is such that the artery is quite close to one surface and far from another. Also, there is a bone in the middle, as well as other blood vessels. Again, we assume the strain equilibrates.

$$\frac{r_o(t) - r_o(0)}{r_0(t)} = \frac{\sigma_\theta(t)}{Ey} - \frac{v(\sigma_r(t) + \sigma_z)}{Ey}$$

One may then write the equations relating stresses to pressures. Note that we are implicitly assuming small displacements, as the unstressed (initial) inside and outside radii are used. We further assume that the cylinder has piston ends. $p_o[t]$ and $p_i[t]$ are used as these are the pressures at equilibrium, not those initially applied.

$$\sigma_r(t) = -p_o(t)$$

$$\sigma_\theta(t) = \frac{2p_i(t) - (k(t)^2 + 1)p_o(t)}{k(t)^2 + 1}$$

$$k(t) = \frac{r_o(0)}{r_i(0)}$$

$$\sigma_z = 0$$

From the above equations one may eliminate the time dependent variables for cuff volume, stresses, radius ratios, and external radius. One then solves the equations for the internal pressure as a function of time. The result is as follows:

$$p_i(t) = -\frac{1}{2}\left(\frac{r_o(0)^2}{r_i(0)^2} + 1\right)\left(\frac{Ey\left(\sqrt{\pi}\,Kwr_o(0) - \sqrt{Kw\left(\frac{\pi Kwr_o(0)^2 + 2V(0)\Delta p_o(t)}{2V(0)\Delta p_o(t)}\right)}\right)}{\sqrt{Kw\left(\frac{\pi Kwr_o(0)^2 + 2V(0)\Delta p_o(t)}{2V(0)\Delta p_o(t)}\right)} + \sqrt{\pi}\,Kwr_o(0)} + (v-1)p_o(t)\right)$$

This form of the equation permits identification of some special cases, which may be used to estimate the parameters to the model.

When $\Delta p_o[t]=0$, i.e. when cuff pressure is at the mean cuff pressure $p_o[t]$. For example, when cuff pressure is set to diastolic pressure, we can assume no pressure augmentation in the artery, so assuming we have measured mean pressure non-invasively, then we know $p_i[t_{mean}]$, $p_o[t_{mean}]=$DBP and can thus find the radius ratio. We can also further assume incompressibility of the soft tissue, in which case $v \to 0.5$. Solving for radius ratio, k, gives:

$$k^2 = \frac{4p_i(t)}{p_o(t)} - 1$$

When $p_i[t]=p_o[t]$, so, for example, when cuff pressure is set to between DBP and SBP, the external radius is dependent on $V[0]$ and $\Delta p_o[t]$ (i.e. pressure fluctuations in the cuff). We again assume incompressibility. Solving for external radius gives:

$$r_o(0)^2 = -\frac{V(0)\Delta p_o(t)(2Ey(k^2+1) + (k^2-3)p_o(t))^2}{4\pi Ey(k^4 - 2k^2 - 3)Kwp_o(t)}$$

One can also get an idea of the form of the relationship between internal pressure and $\Delta po[t]$ by rearranging and simplifying:

$$p_i(t) = -\frac{1}{2}\left(\frac{r_o(0)^2}{r_i(0)^2} + 1\right)\left(Ey\left(\frac{2}{\sqrt{\frac{2V(0)\Delta p_o(t)}{\pi Kwr_o(0)^2} + 1} + 1} - 1\right) + (v-1)p_o(t)\right)$$

It is apparent that this expression takes the form:

$$p_i = c_1/f(\Delta p_o) + c_2 \qquad \text{i}$$

where $c_1$ and $c_2$ are constant relative to $\Delta p_o$ and $p_i$, and f is a power function.

FIG. 4 is a plot of this relationship, ignoring any linear scaling and offset. Using the following physiological values for the variables $$\left\{k \to \sqrt{\frac{7}{5}},\right.$$

Ey→50 Kilo Pascal, K→10.1 Pascal, v→0.5, w→120 Meter Milli, $r_o(0)$→6 Centi Meter, V(0)→100 Liter Milli, $p_o(t)$→150 MillimeterMercury÷133.322 Pascal x, $\Delta p_o(t)$→133.322 Pascal x)

results in the plot of FIG. 5. These plots indicate that $c_1$, $c_2$ and f should be chosen such that increments in $\Delta p_o$ at larger values of $\Delta p_o$ result in smaller increments in $p_i$ than equal increments in $\Delta p_o$ at smaller values of $\Delta p_o$.

Note that the value for bulk modulus, K, is much less than that of air (normally $10^5$ Pa) which corresponds to the fact that the cuff is very conformable and changes in pressure cause changes in volume due to shape changes, rather than compression of the air inside.

It may also be observed that a naïve use of this model does not correctly predict the relationship for subdiastolic cuff pressures. This is probably due to changes in the effective radius ratio for an artery undergoing collapse.

The above model has implications in the design of the waveform sensing cuff device. In particular, the relationship between arterial and cuff pressure oscillation becomes more linear if any of the following occur:

Bulk modulus increases
Cuff internal radius increases
Volume contained in the cuff decreases The amplitude of the pressure oscillations for any given arterial pulse pressure is predicted to increase if any of the following occur:

Bulk modulus increases
Cuff width increases
Cuff internal radius increases
Volume of cuff decreases Determining Parameters of Aortic-Brachial Model The U.S. patent application Ser. No. 12/455,516, filed Jun. 3, 2009. referred to above, discloses a method for reconstructing the central aortic pressure waveform from a suprasystolic, upper-arm, oscillometric signal. The method made use of a model with two parameters, corresponding to a reflection coefficient and the propagation time delay along the subclavian-axillary artery.

This previous application mentioned the potential to identify these parameters from additional measurements, for example, the use of a heart-sounds sensor to estimate the entry of a pressure pulse into the subclavian artery.

The present invention provides additional methods for the determination of parameters to the model of wave propagation between the aorta and the cuff.

As already discussed, a heart sounds sensor could be employed. This detects the time of the valve closure. By estimating the systolic duration from the brachial waveform, we may estimate the start of systole.

A tonometer of some sort may be applied to the subclavian or carotid artery. This would allow detection of the onset of the pressure wave as it passed the location of the tonometer, which would be close to the start of the subclavian artery.

An ECG may be used to determine the R-wave, which corresponds to depolarization of the cardiac muscle in preparation for the ejection phase.

The above methods allow estimation of the time delay parameter. Disclosed below is another method using a system of two (or more) cuffs (one more proximal to the heart) that allows the estimation of time delay or reflection coefficient.

The relationship between central pressure, $p_{to}$ and pressure at the proximal cuff $p_{t3}$ is given by $$p_{t0}(t) = \frac{bp_{t3}(t-dt)}{b+1} + \frac{p_{t3}(t+dt)}{b+1}$$

One may write a similar equation for the pressure at the distal cuff $p_{t4}$, where the additional propagation delay from the proximal to the distal cuff is given by $\delta t$.

$$p_{t0}(t) = \frac{bp_{t4}(-dt+t-\delta t)}{b+1} + \frac{bp_{t4}(dt+t+\delta t)}{b+1}$$

In the time domain, one may solve the above equations for the reflection ratio directly:

$$b \to \frac{p_{t4}(dt+t+\delta t) - p_{t3}(dt+t)}{p_{t3}(t-dt) - p_{t4}(-dt+t-\delta t)}$$

$\delta t$ may be estimated by another method, for example, one of the methods given above.

In the complex frequency (Laplace) domain, one may write the original equations as:

$$P_{t0}(s) = \frac{be^{-dts}P_{t3}(s)}{b+1} + \frac{e^{dts}P_{t3}(s)}{b+1}$$

$$P_{t0}(s) = \frac{be^{s(-dt-\delta t)}P_{t4}(s)}{b+1} + \frac{e^{s(dt+\delta t)}P_{t4}(s)}{b+1}$$

This makes it possible to solve the equations for the time delay (or reflection coefficient) directly, to obtain the following result:

$$e^{2dts} = \frac{b(P_{t3}(s) - e^{-s\delta t}P_{t4}(s))}{e^{s\delta t}P_{t4}(s) - P_{t3}(s)}$$

It can be seen that either the time delay or the reflection coefficient may be easily determined in the frequency domain. Furthermore, if more than two cuffs are used, then both parameters may be determined from the cuff assembly applied to the upper arm without resorting to heart sounds sensors, tonometers or other sensor types placed elsewhere on the body.

Estimation of Forward and Backward Propagating Components

Various ones of the prior patent applications, referred to above, disclose methods to reconstruct an estimate of the central pressure waveform from a peripheral arterial signal measured under specific conditions.

It is commonly understood that this central aortic pressure waveform (measured or estimated by whatever method) represents a superposition of a forward going (ejection) wave down the aorta, and a reflected wave returning from the iliac bifurcation (or thereabouts). Other proposed models use compliance and resistance elements to try to explain the shape of the pressure waveform. In all these cases, the estimation of model parameters is either difficult or does not work well.

According to the present invention, it is possible to improve on these methods by recognizing that the aortic system is not time invariant. In particular, valve closure at the end of systole introduces a marked change in the reflection of waves within the aorta. Specifically, prior to the valve closure, the wave reflected from the distal aorta is able to enter the heart and due to the shape of the heart does not significantly reflect back into the aorta. However, once the valve closes, the wave reflected from the distal aorta is re-reflected from the valve, which is a sudden change in impedance. This increases the total pressure within the aorta and contributes to the size of the dicrotic notch. Our research has shown that without accounting for this additional reflection, simulated pressure waves are morphologically unsatisfactory representations of measured pressure waveforms.

Accounting for this non-stationary behavior allows one to perform more complete analysis on central pressure waveforms, including the following:

Decompose forward and reflected pressure waves

Identify dynamics of valve closure, potentially including valve insufficiency.

Calculate the residual pressure waves (from the previous heart beat)

Estimate pressure decay due to systemic vascular resistance

Approximate the flow waveform and hence relative stroke volume.

The total, observed, central pressure waveform for any single heart beat is a superposition of the following components:

Residual pressure, caused by the static extension of the arteries with the blood volume Exponentially decaying pressure generated by previous heart beats (generally only the one previous is of significance)

The pressure generated by the heart in that pulse (incident wave)

The incident wave pressure reflected from the distal aorta (mostly the iliac)

The distal reflection again reflected from the aortic valve (when closed)

The means of calculating these components is given in the Detailed Description of Preferred Embodiment.

Estimation of Aortic Blood Flow Waveforms

Now that we have estimated the forward and backward going components of the waveform, we may estimate the pressure waveform at other positions in the aorta by merely advancing or retreating the components as appropriate, and then summing these components.

This also allows us to estimate the flow waveform, which we assume is made up of two superimposed components (1) an ejection of volume from the heart, $v_{Incident}$, and (2) an augmentation or reduction of flow due to the pressure differential across a segment of the aorta, $\Delta v$. For example, if pressure downstream is higher than pressure upstream, then the net force acts on the volume of blood in between to impede flow. Conversely, if the proximal pressure is higher than the distal pressure then the net force acts to enhance flow.

Stroke volume is then the integral of the flow curve found by summation of these two components over one heart beat. Vascular resistance may be estimated based on the pressure-flow relationship.

For a full understanding of the present invention, reference should now be made to the following detailed description of the preferred embodiments of the invention as illustrated in the accompanying drawings.

BRIEF DESCRIPTION OF THE DRAWINGS

FIG. 3 is a time diagram showing a single representative aortic pressure waveform and constituent pressure waveforms, being the incident wave and iliac reflection wave, and indicating certain cardiovascular medical parameters which are determined according to the invention.

FIG. 4 is a graph showing the relationship between the normalized oscillatory component of pressure in an external cuff, $\Delta p_o(t)$, and the normalized intra arterial pressure, $p_i(t)$.

FIG. 5 is a graph showing a relationship between the oscillatory component of pressure in an external cuff, $\Delta p_o(t)$, and the intra arterial pressure, $p_i(t)$, having assumed physiologically reasonable values for model parameters.

FIGS. 6-15 are screen shots each showing four plots illustrating the estimation of the pressure and flow waveforms from a measured pressure waveform.

Figure 1:
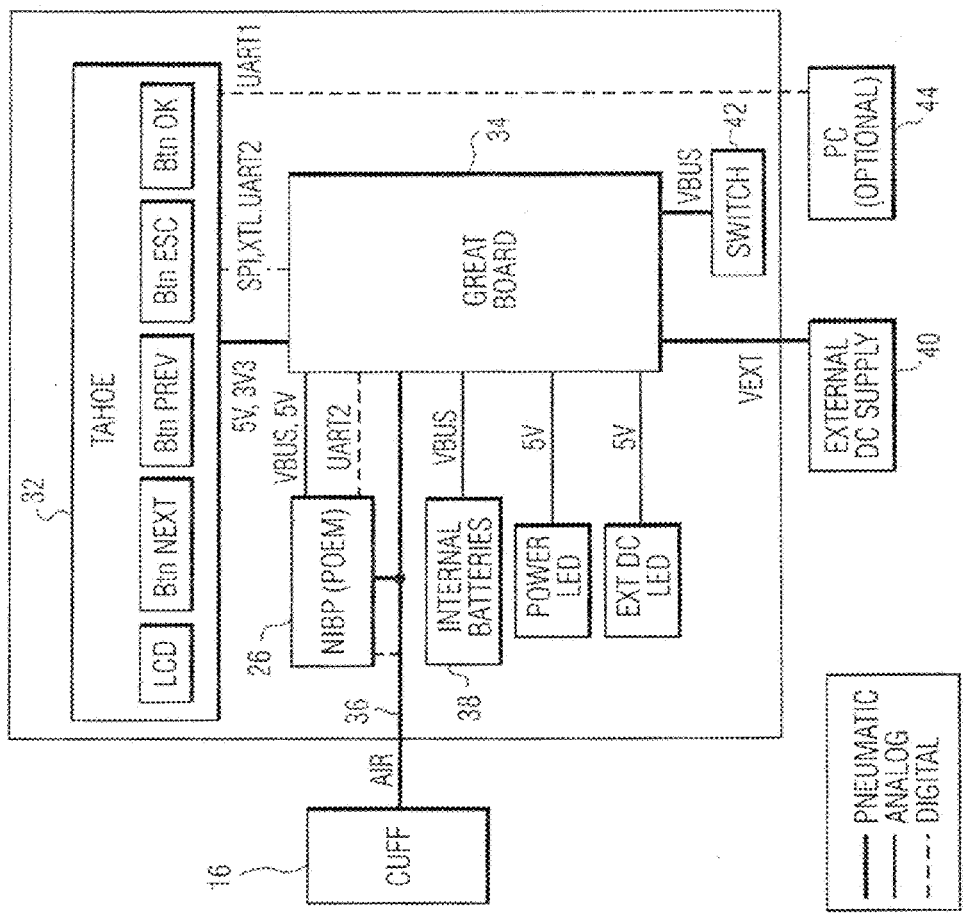
FIG. 1 is a block diagram showing the preferred embodiment of apparatus according to the invention for obtaining supra-systolic signals from a blood pressure cuff and determining from these signals certain cardiovascular medical parameters which are useful in diagnosing and treating cardiovascular disease.

The top left chart of each screen shot shows the original (measured) pressure wave, the calculated forward and reflected pressure waveform components and the estimated pressure wave found by summing the component pressure waveforms.

The bottom left chart of each screen shot shows the normalized component pressure waveforms, and the reflection coefficient associated with valve closure.

The top right chart of each screen shot shows the estimated pressure waveform at the original location (labeled root) and the reconstructed pressure waveform at a distance down the aorta.

The bottom right chart of each screen shot shows the estimated total flow wave and the constituent flow waves being the incident wave generated by the heart, and the differential wave calculated from the difference between the root and at distance pressure waveforms.

FIGS. 6 to 10 correspond to a first human subject given phenylephrine during epidural anaesthesia with propofol sedation, measured at baseline (FIG. 6), after sedation (FIG. 7), soon after inflation of a tourniquet (FIG. 8), a period of time after inflation of the tourniquet (FIG. 9), and two minutes after deflation of the tourniquet (FIG. 10)

FIGS. 11 to 15 correspond to a first human subject given ephedrine during epidural anaesthesia with propofol sedation, measured at baseline (FIG. 11), after sedation (FIG. 12), soon after inflation of a tourniquet (FIG. 13), a period of time after inflation of the tourniquet (FIG. 14), and two minutes after deflation of the tourniquet (FIG. 15)

FIG. 16 is a flow chart of the steps taken to decompose a central pressure waveform.

FIG. 17 shows the constituent waves found by decomposition of a central pressure waveform.

FIG. 18 shows how constituent pressure waves are shifted in time to reconstruct the total pressure at a distance down the aorta.

FIG. 19 shows a preferred embodiment of sensors, including proximal and distal cuffs and a heart sounds sensor.

FIG. 20 is a flow chart describing the steps taken to measure the information required to calculate parameters to a model relating aortic and brachial pressures.

FIG. 21 is a diagram showing the relationship between heart activity sensor signals and cuff oscillation signals.

FIG. 22 is a diagram showing the relationship between heart sounds sensor signals and cuff oscillation signals for proximal and distal cuffs.

FIG. 23 is a block diagram of apparatus used to make measurements required to calculate parameters to a model relating aortic and brachial pressures.

FIG. 24 is an overall flow diagram showing the relationship between various aspects of this invention.

FIG. 25 is a diagram showing an exponential decay fitted to the diastolic portion of a total pressure waveform.

FIG. 26 is a diagram showing incident and reflected wave components of an aortic pressure waveform.

FIG. 27 is a diagram showing primary and secondary reflected wave components of an aortic pressure waveform.

DETAILED DESCRIPTION OF THE PREFERRED EMBODIMENTS

The preferred embodiments of the present invention will now be described with reference to FIGS. 1-27 of the drawings. Identical elements in the various figures are designated with the same reference numerals.

This invention concerns 1) the estimation of intra-arterial brachial blood pressure waveforms from the pressure oscillations in a brachial blood pressure cuff; 2) the estimation of parameters to a model relating the intra-arterial brachial blood pressure waveform to the aortic blood pressure waveform; 3) the estimation of forward and backward propagating components of the aortic blood pressure waveform from the aortic blood pressure waveform; and 4) the estimation of aortic blood flow waveforms from the forward and backward propagating components of the aortic blood pressure waveform. The relationship between these parts of the invention are shown in FIG. 24. FIG. 24 shows how estimation of intra-arterial brachial blood pressure waveforms are used to estimate parameters relating brachial and aortic blood pressure waves, which are in turn used to estimate the aortic pressure wave, which is in turn used to estimate forward and backward propagating components of the aortic pressure wave, which are in turn used to estimate the aortic blood flow wave.

Estimation of Intra-Arterial Brachial Blood Pressure Waveforms.

Figure 2:
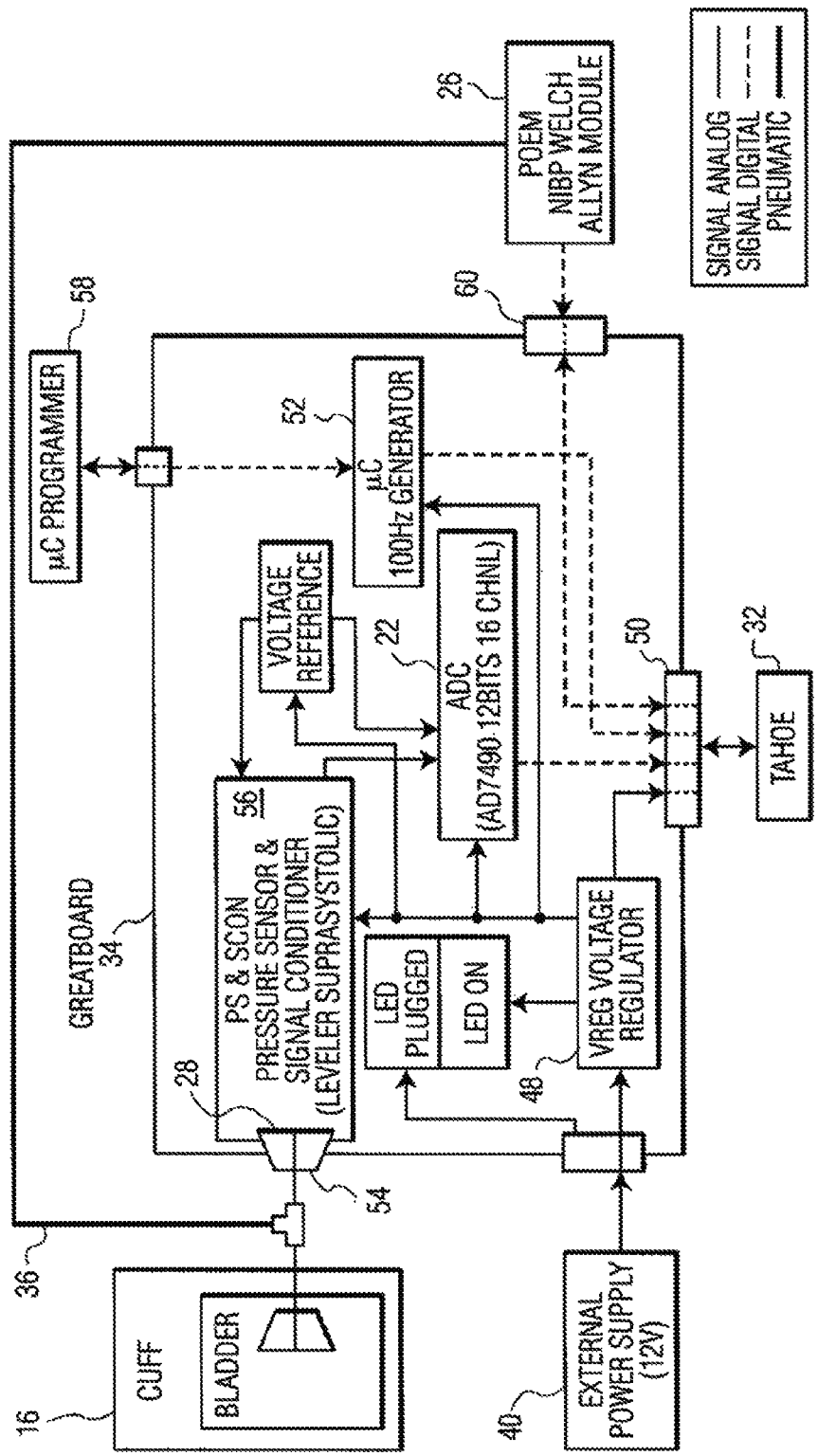
FIG. 2 is a more detailed block diagram of the apparatus of FIG. 1.

FIGS. 1 and 2 are block diagrams of a preferred embodiment of the oscillometric apparatus according to the invention. The apparatus is controlled by an embedded central processing unit ("CPU") designated as Tahoe 32. Tahoe 32 interfaces with a "great board" 34, which in turn is connected to the other components of the apparatus. The great board 34 contains custom signal processing electronics (as further explained below), and is connected to cuff 16 by pneumatic connector 36. Pneumatic connector 36 also connects NIBP measurement module 26 which controls the pneumatic pressure in cuff 16 and achieves and maintains the proper pressure in cuff 16. NIBP measurement module 26 can be a commercially available unit, such as supplied by Welch Allyn under the name POEM. NIBP measurement module 26 is electronically connected to great board 34, which inputs the pre-determined supra-systolic pressure information to the module 26. As shown in FIG. 1, the apparatus contains internal batteries 38 and an external DC power supply 40, and is operated by switch 42. The apparatus can optionally be connected to a PC 44, interfaced through the Tahoe 32.

FIG. 2 illustrates further detail of the components of the great board 34. Generally, the great board 34 contains components relating to power regulation and supply 48, an interface 50 to the Tahoe board 32, an interface 60 to NIBP measurement module 26, and a 100 Hz generator 52 for pacing A/D converter 22. Also, great board 34 comprises pneumatic interface 54 for pneumatic connection through pneumatic connecter 36 to cuff 16. Pneumatic interface 54 is connected to pressure sensor 28 within great board 34, which measures the cuff pulse waves and provides a transduced analog signal to signal conditioner ("SCON") 56. The output analog signal of SCON 56 is input into A/D converter 22 where it is converted into a digital signal and passed to the Tahoe 32. A/D converter 22 can be a 12 bit 16 channel A/D converter, such as AD7490. The programmer device 58 is used to load firmware into the microcontroller 52 when the equipment is manufactured.

The Tahoe 32 comprises a dedicated CPU which performs computations on the digitized pulse waveform signals received from the A/D converter to produce, store and display a representative cardiac pulse waveform of the type shown in FIG. 3.

The Tahoe 32 then performs additional computation on the digitized pulse waveform $\Delta p_o$ to calculate an estimated intra-arterial blood pressure waveform $p_i$ using a relationship such as the one shown in FIG. 5.

Determining Parameters of Aortic-Brachial Model

In the preferred embodiment, measured brachial intra-arterial blood pressure waveforms are used to estimate the pressure waveform at the subclavian root in the aorta, $p_{to}(t)$. In this model, $p_{to}(t)$ is related to a proximal and distal brachial pressure as shown in FIG. 19 by the formulae:

$$p_{to}(t) = b/(b+1) p_{t3}(t-dt) + 1/(b+1) p_{t3}(t+dt)$$

$$p_{to}(t) = b/(b+1) p_{t4}(t-dt-\delta t) + 1/(b+1) p_{t4}(t+dt+\delta t)$$

The parameters to these formulae are determined using the apparatus described by the block diagram of FIG. 23. In the preferred embodiment, the measurement of signals from the proximal and distal suprasystolic cuffs is carried out according to the steps shown in FIG. 20. First both cuffs are inflated to a suprasystolic pressure. The intra-arterial pressure waves within the brachial artery thus first impinge on the proximal cuff. Recordings of proximal cuff pressure oscillations and heart activity is made. The proximal cuff is then deflated to a subdiastolic pressure, allowing the intra-arterial pressure waves to impinge on the distal cuff. Measurements of the distal cuff pressure oscillations and heart activity are made. Both cuffs are then fully deflated, to prevent ischaemia.

The apparatus described is thus used to provide the following signals. The Proximal Suprasystolic Cuff provides a signal that is used to estimate the intra-arterial pressure $p_{t3}$ and the Distal Suprasystolic Cuff provides a signal that is used to estimate the intra-arterial pressure $p_{t4}$. The Heart Activity Sensor, which is preferably a heart sounds sensor, provides a reference signal $a_3$ and $a_4$ that is common to both proximal and distal measurements. This is shown in FIG. 22. Measurements from the Heart Activity Sensor allows the calculation of the propagation time $\delta t$ between proximal and distal cuffs. This is also shown in FIG. 22. The time for a pressure wave to propagate from the subclavian root to the proximal cuff, dt, is determined by calculating the difference between the time of the heart sounds and the time of the dicrotic notch on the proximal intra-arterial pressure waveform. This is illustrated in FIG. 21. The reflection coefficient b is then calculated using the formula $$b = \frac{p_{t4}(dt+t+\delta t) - p_{t3}(dt+t+\delta t)}{p_{t3}(t-dt) - p_{t4}(-dt+t-\delta t)}$$

The result of these measurements and calculations is that all the parameters to the model relating brachial and aortic pressure waveforms are known and the aortic pressure waveform $p_{to}(t)$ can be calculated.

Estimation of Forward and Backward Propagating Components

The next step in the invention is to decompose the total aortic pressure waveform $p_{to}(t)$ into estimated forward and backward travelling wave components. This proceeds according to the steps shown in FIG. 16.

From the central blood pressure waveform, P, we first find the diastolic portion. From this we can calculate an exponential decay of the form:

$$P[n+1] - P_{Res} = \gamma(P[n] - P_{Res})$$

Where n are sample indices, and $\gamma$ and $P_{Res}$ are the parameters that fit the diastolic portion to the exponential decay curve. $\gamma$ indicates the rate at which pressure is decaying, and $P_{Res}$ is the steady state pressure that would be reached without subsequent heart beats.

One may thus determine the component of the waveform contributed by the previous heart beat, assuming exponential decay of the pressure at the end of the previous beat as shown in FIG. 25.

$$P_{Decay}[n] = \gamma P_{Decay}[n-1]; \quad P_{Decay}[0] = P[0] - P_{Res}$$

One then assumes a particular form of the pressure wave generated by the heart. A suitable form, based on LV pressure waveforms, is a power of a half-sine wave, with a period double that of the systolic ejection period (SEP), i.e.:

$$P_{Incident} = \sin(\pi t / SEP)^\epsilon \quad 0 < t < SEP$$

The exponent $\epsilon$ is determined based on the slope of the observed central pressure waveform, in order to give a reasonable approximation of the initial gradient.

The incident wave is reflected from the distal aorta, and this reflection can be modeled by an impedance $Z_{AO}$ based on the approximate geometry and material properties of the aorta. As will be seen, the absolute magnitude of the reflection wave need not be known. A suitable reflection model can be represented as an infinite impulse response digital filter. One sufficient example is the following:

$$P_{Iliac}[n] = P_{Incident}[n-\delta] + \gamma P_{Iliac}[n-1]$$

where $\delta$ is related to the time of the principal reflection. The incident and reflected waves are shown diagrammatically in FIG. 26.

This reflected wave is again reflected from the aortic valve. This reflection only occurs when the valve is closed, i.e. the diastolic portion, as shown in FIG. 27. The reflection coefficient at the valve is thus non-stationary. A suitable approximation may be employed, such as a sigmoid function with a transition at the time of the dicrotic notch.

$$R(t)=1/(1+e^{-\sigma t+SEP})$$

Windowing the distal reflection with this sigmoid function gives the pressure waveform of the secondary reflection.

$$P_{Valve}(t)=P_{Iliac}(t)R(t)$$

Once all these components (basis functions) have been identified, we may use principles of superposition to calculate a best-fit, $P_{Est}$ to the original central pressure waveform, P, with parameters α and β.

$$P_{Est}=P_{Res}+\alpha P_{Incident}+\beta(P_{Iliac}+P_{Valve})+P_{Decay}$$

An example of this curve fitting is shown in FIG. 17.

As an additional, optional step, we may refine our estimate of the shape of the incident pressure wave by apportioning the difference between estimated and observed pressures to the estimate of the incident pressure waveform and then recalculating $P_{Iliac}$ and $P_{Valve}$ as above.

$$P_{Incident}(t) \leftarrow \alpha P_{Incident}(t)-(P_{Est}(t)-P(t))\alpha/(\alpha+\beta)(1-R(t))$$

Estimation of Aortic Blood Flow Waveforms

Now that we have estimated the forward and backward going components of the waveform, the total pressure waveform $P_{Est,\delta x}(t)$ at a distance δx downstream from the original position in the aorta is calculated by advancing or retreating the components calculated previously as appropriate by a time δt, and then summing these components.

$$P_{Est,\delta x}(t)=P_{Res}+\alpha P_{Incident}(t-\delta t)+\beta(P_{Iliac}(t+\delta t)+P_{Valve}(t-\delta t))+P_{Decay,\delta x}$$

The distance δx is equal to the product of wave speed and δt.

The flow waveform is then calculated as the sum of (1) an ejection of volume from the heart, $v_{Incident}$, and (2) an augmentation or reduction of flow due to the pressure differential across a segment of the aorta, Δv.

Euler's law for incompressible flow is used to calculate Δv according to the following:

$$\Delta v(t)=\upsilon_1(P_{Est}(t)-P_{Est,\delta x}(t))$$

$\upsilon_1$ is a scaling factor related to aortic cross section. We assume that the flow due to ejection, $v_{Incident}$, can be approximated by the difference between the incident pressure wave (acting within the ventricle) and the iliac reflection wave (acting outside the ventricle).

$$v_{Incident}(t)=\upsilon_2(P_{Incident}(t)-P_{Iliac}(t))(1-R(t))$$

$\upsilon_2$ is another scaling factor from Euler's equation. The total flow rate is then given by:

$$V(t)=v_{Incident}(t)+\Delta v(t)$$

Medical Utility of Calculated Parameters

Various cardiovascular medical parameters which are determined by the method and apparatus of the present invention are set forth and illustrated in FIG. 3. Those commonly known to a medical practitioner are:

Systolic pressure, $p_{Sys}$, which is determined as the maximum of the estimated total pressure waveform, $p_{t0}$.

Diastolic pressure, $p_{Dia}$, which is determined as the minimum of the estimated total pressure waveform.

Mean pressure, $p_{Mean}$, which is determined as the time-average of the estimated total pressure waveform.

Systolic ejection period, SEP, which is the time from the start of the pressure wave to the dicrotic notch.

Contractility, $dP/dt_{max}$ (not shown) which is the maximum rate of change of the total pressure.

Stroke volume, SV, which is determined as the integral of the estimated flow waveform over one heart beat.

Further cardiovascular medical parameters are made available by this invention which are not commonly known or measured by medical practitioners. They are:

Aortic incident pulse pressure, α. This is the pressure differential generated by the heart during systole, and is different than the maximum pressure experienced by the arteries during systole, which would be the systolic pressure.

Aortic reflected wave pressure, β. This is the maximum amplitude of the reflected pressure wave in the aorta, and corresponds to a force against which the heart must work. It is also related to the impedance (i.e. stiffness) of the aorta.

Aortic reflected wave ratio, β/α. This is a relative measure of the size of the reflected pressure wave. It is similar to augmentation index, but is calculated from the wave components, not the wave morphology, and thus is a better representation of arterial stiffness. Instead of using the amplitudes α and β, areas under the incident and reflected wave curves, or other measures of wave amplitude could be used.

Reserve pressure, $p_{Res}$. This is the pressure to which the arterial system would trend if no further heart beats were experienced, and there was no drainage to the venous system. That is, it is the pressure caused by the elastic arteries compressing the blood volume. It is a measure of the baseline elasticity and blood volume of the subject.

Decay rate, γ. This is a measure of the rate at which pressure in the arterial system dissipates. The dissipation of pressure energy primarily occurs is vascular resistive elements, thus decay rate is a measure of systemic vascular resistance.

FIGS. 6 to 15 illustrate how the cardiovascular medical parameters may be used, with two drug therapies, to assess the cardiovascular performance of a patient. As will be explained below, the parameters provide useful information especially when they are determined multiple times to generate historical data.

EXAMPLES

The following examples have been taken from knee replacement operations by two protocols under epidural anesthesia with propofol sedation. During the operation a thigh tourniquet was applied. In the first protocol, the patient was given a continuous phenylephrine infusion to maintain systolic pressure between 100 and 130 mmHg. In the second protocol, the patient was given ephedrine rather than phenylephrine.

Both propofol and the epidural anesthesia have a vasodilating effect, which is also expected after deflation of the thigh tourniquet. Phenylephrine is a vasoconstrictor with little effect on cardiac contractility, whereas ephedrine acts as both a vasoconstrictor and cardiac stimulant.

The central waveform has been estimated from the supra-systolic, oscillometric waveform in each case, using the same parameters for shape correction, propagation delay and cuff reflection coefficient. The scaling of oscillometric pressure to arterial pressure was the same for all cases.

A summary of the main results is as follows:

|  |  | Baseline | After Propofol Induction | 10 min post tourniquet down | Pre tourniquet down | 2 min post tournequet down |
|---|---|---|---|---|---|---|
| BP (mmHg) | Phenyl | 104/75 | 105/75 | 110/73 | 111/72 | 107/70 |
|  | Ephed | 106/71 | 106/71 | 106/71 | 108/73 | 111/76 |
| PR (bpm) | Phenyl | 88 | 82 | 55 | 57 | 74 |
|  | Ephed | 83 | 82 | 90 | 89 | 92 |
| SEP (s) | Phenyl | 0.26 | 0.31 | 0.35 | 0.35 | 0.34 |
|  | Ephed | 0.28 | 0.34 | 0.32 | 0.32 | 0.26 |
| $dP/dt_{max}$ (mmHg/s) | Phenyl | 503 | 382 | 369 | 334 | 465 |
|  | Ephed | 514 | 539 | 514 | 562 | 623 |
| Incident Pulse Pressure (mmHg) | Phenyl | 28 | 27 | 26 | 28 | 33 |
|  | Ephed | 29 | 31 | 30 | 32 | 33 |
| Reflected Wave Ratio (%) | Phenyl | 23 | 23 | 53 | 47 | 30 |
|  | Ephed | 34 | 26 | 26 | 15 | 10 |
| Relative SV (mL) | Phenyl | 49 | 56 | 58 | 66 | 75 |
|  | Ephed | 58 | 63 | 59 | 67 | 62 |
| Relative CO (L/min) | Phenyl | 4.4 | 4.6 | 3.2 | 3.8 | 5.6 |
|  | Ephed | 4.9 | 5.2 | 5.3 | 6 | 5.7 |

It can be seen that the results, calculated using the disclosures in this invention, conform to those expected. Namely:

Systolic and diastolic pressures are roughly similar under this protocol.

Pulse rate decreases significantly on administration of phenylephrine, and increases slightly with ephedrine. In both cases, pulse rate increases after the tourniquet is deflated.

Propofol anaesthesia increases systolic ejection period.

Contractility decreases markedly under the phenylephrine protocol but is stable under the ephedrine protocol. In both cases, contractility increased after tourniquet deflation.

Reflection ratio increased markedly with phenylephrine, but decreased under the ephedrine protocol (due to a combination of propofol and epidural anaesthesia)

Stroke volume increased under the phenylephrine protocol, but this is expained by the increase in systolic ejection period and decrease in pulse rate (i.e. greater diastolic filling time). Stroke volume remained largely constant under the Ephedrine protocol.

Cardiac output decreased significantly under the phenylephrine protocol but increased somewhat in response to the ephedrine protocol.

In summary, the present invention provides methods for processing pressure signals received from an inflated blood pressure cuff which include:

A way of non-linearly scaling cuff pressure oscillations to create a pseudo-arterial waveform. The method is based on a physical model such that its parameters may be determined from particular cuff configurations. The model may also be used to help guide and optimize cuff designs.

A way of using a proximal and distal cuff for suprasystolic measurement in a manner that allows calculation of parameters for a model to more accurately estimate the central pressure waveform. The method may be augmented by or augment other sensing techniques such as tonometers, ECG or heart sounds sensors to more completely or accurately define the model parameters. The method may operate in either the time or frequency domains to calculate such parameters. More than two cuffs may be employed.

A way of decomposing a central pressure waveform into incident and reflected components, based on a non-stationary model of the aortic valve reflection coefficient and its effect on the dicrotic notch. The method allows the calculation of incident, distal aortic reflection, aortic valve reflection, previous beat decay and residual pressures. From these components, physiologically meaningful parameters may be calculated such as incident wave height and a true reflection ratio, as opposed to the morphology-driven (and confounded) augmentation index parameters.

A way of utilizing the above pressure wave components to reconstruct the total pressure waveform at various points in the aorta and the left ventricle, and using these pressure gradients in conjunction with Euler's equations for incompressible fluids to estimate blood flow, including the flow waveform, stroke volume and cardiac output. Further vascular parameters may then be calculated including systemic resistance.

There has thus been shown and described a novel method and apparatus for producing a central pressure waveform in an oscillometric blood pressure system which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A method of estimating an internal, central arterial blood pressure waveform from pressure waveforms obtained from at least one blood pressure cuff placed at two locations along a brachial artery of a patient's arm, based on a physical model of the artery, said method comprising the steps of:
   a. inflating a proximal blood pressure cuff on the artery of the arm to a supra-systolic pressure;
   b, sensing a proximal cuff pressure waveform associated With at least one cardiac ejection cycle;
   c. inflating a distal blood pressure cuff on the artery of the arm to a supra-systolic pressure;
   d. sensing a distal cuff pressure waveform associated with at least one cardiac ejection cycle;
   e. using a processor, calculating the time of propagation of a blood pressure pulse from the entry of the said artery to the proximal cuff;

f. using said processor, calculating the time of propagation of a blood pressure pulse from the proximal cuff to the distal, cuff;

g. using said processor, calculating a reflection coefficient a blood pressure pulse at at least one of the proximal and distal cuffs; and h. based on said physical model of wave propagation along said artery between an aorta and said proximal and distal blood pressure cuffs and using said processor, determining an estimated internal, central arterial blood pressure waveform at the opening of the said artery.

2. The method of claim 1, where the time of propagation of said blood pressure pulse from the proximal cuff to the distal cuff is calculated by taking the difference in time between the incidence of the blood pressure pulse at the proximal cuff and an identifiable point on a signal related to heart activity, taking the difference in time between the incidence of the blood pressure pulse at the distal cuff and an equivalent identifiable point on the same signal related to heart activity, and calculating the difference between the differences.

3. The method of claim 2, where the signal related to heart activity is measured using one of an ECG, heart sounds sensor, tonometer, photoplethysmograph and blood pressure cuff.

4. The method of claim 1, where the time of propagation of said blood pressure pulse from the entry of the said artery to the proximal cuff is calculated by taking the difference in time between the incidence of the blood pressure pulse at the proximal cuff and an identifiable point on a signal related to the entry of a pressure pulse into the subclavian artery.

5. The method of claim 1, where the time of propagation of said blood pressure pulse from the entry of the said artery to the proximal cuff is calculated using a ratio of differences between frequency-domain representations of the proximal and distal pressure waveforms.

6. The Method of claim 5, where the ratio is given by:

$$dt = 1/2s \, \ln\left(\frac{b(P_{t3}(s)) - \exp(-s\delta t)P_{t4}(s)}{\exp(s\delta t)P_{t4}(s) - P_{3t}(s)}\right)$$

where dt is the time of propagation of said blood pressure pulse from the entry of the said artery to the proximal cuff, $P_{t4}$ is the pressure at the distal cuff as a function of complex frequency, $P_{t3}$ is the pressure at the proximal cuff as a function of complex frequency, b is the pressure wave reflection coefficient, $\delta t$ is the time for the pressure wave to propagate from the proximal to the distal cuff, and s specifies a complex frequency coordinate.

7. The method of claim 4, where the signal related to heart activity is measured using one of a tonometer and a strain sensor, placed over one of the subclavian artery, and a carotid artery.

8. The method of claim 4, where the signal related to heart activity is measured using a heart sounds sensor, and the identifiable point is a time equal to the systolic ejection period prior to the incidence of the heart sounds.

9. The method of claim 4, where the signal related to heart activity is measured using an ECG, and the identifiable point is a predetermined time after the incidence of the R-wave.

10. The method of claim 1, where the reflection, coefficient of the pressure pulse at the proximal cuff is calculated according to a ratio between differences between time-shifted signals calculated from the cuff pressure waveforms.

11. The method of claim 10 where the ratio is given by:

$$b = \frac{p_{t4}(dt + t + \delta t) - p_{t3}(dt + t + \delta t)}{p_{t3}(t - dt) - p_{t4}(-dt + t - \delta t)}$$

where b is the reflection coefficient, $p_{t4}$ is the pressure at the distal cuff as a function of time, $p_{t3}$ is the pressure at the proximal cuff as a function of time, dt is the time for the pressure wave to propagate from the root of the subclavian artery to the proximal cuff, $\delta t$ is the time for the pressure wave to propagate from the proximal to the distal cuff, and t specifies a time coordinate.

12. The method of claim 1, where the reflection coefficient is a predetermined value.

13. The method of claim 1, where the time of propagation of said blood pressure pulse from the entry of the said artery to the proximal cuff is a predetermined value.

* * * * *